(12) United States Patent
Pugin et al.

(10) Patent No.: US 7,589,196 B2
(45) Date of Patent: Sep. 15, 2009

(54) AMINE-SUBSTITUTED BIPHENYLDIPHOSPHINES

(75) Inventors: Benoît Pugin, Münchenstein (CH); Pierre Martin, Rheinfelden (CH); Markus Müller, Stein (CH); Frédéric Maurice Naud, Huningue (FR); Felix Spindler, Starrkirch-Wil (CH); Marc Thommen, Nuglar (CH); Gianpietro Melone, Möhlin (CH); Martin Kesselgruber, Basel (CH)

(73) Assignee: Solvias AG, Basel (CH)

( * ) Notice: Subject to any disclaimer, the term of this patent is extended or adjusted under 35 U.S.C. 154(b) by 484 days.

(21) Appl. No.: 10/552,066

(22) PCT Filed: Apr. 5, 2004

(86) PCT No.: PCT/EP2004/050439

§ 371 (c)(1),
(2), (4) Date: Oct. 5, 2005

(87) PCT Pub. No.: WO2004/089920

PCT Pub. Date: Oct. 21, 2004

(65) Prior Publication Data

US 2006/0276643 A1 Dec. 7, 2006

(30) Foreign Application Priority Data

Apr. 7, 2003 (CH) .................... 0624/03

(51) Int. Cl.
 *C07D 265/36* (2006.01)
(52) U.S. Cl. .......... 544/105; 568/17; 548/101; 548/215; 556/137; 544/64
(58) Field of Classification Search ........ 544/105, 544/64; 568/17; 548/101, 215; 556/137
See application file for complete search history.

(56) References Cited

U.S. PATENT DOCUMENTS

| 4,556,740 | A | 12/1985 | Hansen et al. |
| 5,872,273 | A * | 2/1999 | Saito et al. ............ 556/21 |
| 6,281,390 | B1 | 8/2001 | Pugin et al. |
| 2001/0056210 | A1 | 12/2001 | Pugin et al. |
| 2003/0120122 | A1 | 6/2003 | Pugin et al. |

FOREIGN PATENT DOCUMENTS

| EP | 0 850 945 | 11/2002 |
| EP | 1 002 801 | 6/2003 |

OTHER PUBLICATIONS

Rudolf Schmid et al., "New Developments in enantioselective hydrogenation", Pure & Applied Chemistry, vol. 68, No. 1, pp. 131-138, XP000884387, ISSN: 0033-4545, 1996.

* cited by examiner

Primary Examiner—Shailendra Kumar
Assistant Examiner—Sudhakar Katakam
(74) Attorney, Agent, or Firm—Wenderoth, Lind & Ponack, L.L.P.

(57) ABSTRACT

1,1'-Biphenyl-2,2'-diphosphines having at least one amine substituent in the para position relative to the phosphine group and having the formulae

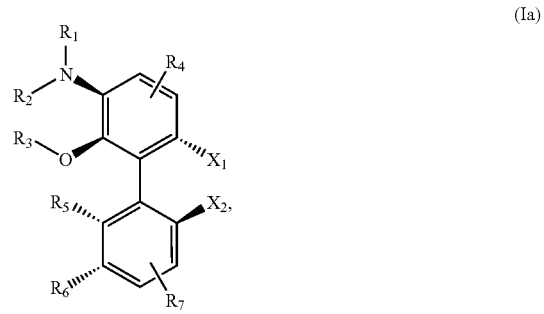

(Ia)

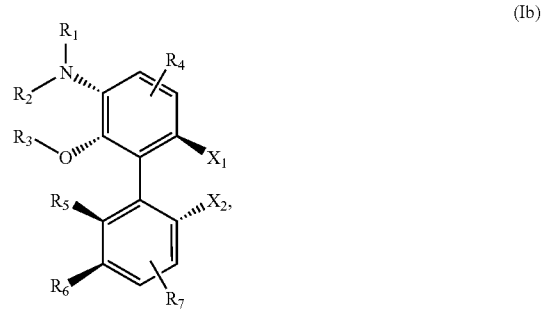

(Ib)

are ligands for metal complexes which serve as catalysts for asymmetric addition reactions of prochiral organic compounds and whose catalytic properties can be tailored specifically to particular substrates by substitution of the amine group.

6 Claims, No Drawings

AMINE-SUBSTITUTED BIPHENYLDIPHOSPHINES

The present invention relates to biphenyldiphosphines having at least one amine substituent in the para position relative to the phosphine group, a process for preparing them, intermediates, metal complexes with these diphosphines as catalysts for enantioselective syntheses and the use of the metal complexes for enantioselective syntheses.

Chiral biaryl-1,1'-diphosphines are an important class of ligands for metal complexes as catalysts for enantioselective syntheses. Ruthenium and rhodium complexes have been found to be particularly useful for enantioselective hydrogenation and rhodium complexes have been found to be particularly useful for enantioselective isomerizations. Some examples of known chiral biaryl-1,1'-diphosphines as ligands in metal complexes are BINAP (cf. S. Akutagawa, Applied Catal. A: General 128 (1995) 171) of the formula (A), Bis-benzodioxanPhos (C.-C. Pai, Y.-M. Li, Z.-Y. Zhou, A. S. C. Chan, Tetrahedron Lett., 43 (2002) 2789) of the formula (B), and diphosphines of the formula (C) described in EP-A-0 850 945:

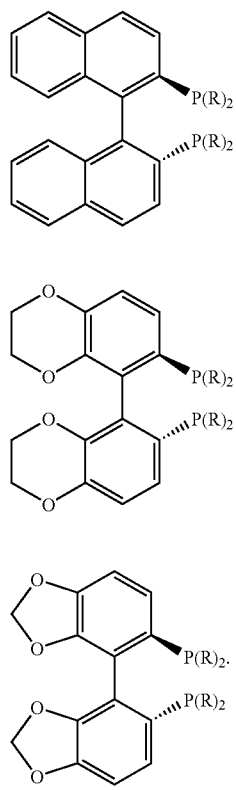

Mention may also be made of the following examples of functionalized biaryldiphosphine ligands of the formulae (D), (E) and (F); see D. J. Bayston, J. L. Fraser, M. R. Ashton, A. D. Baxter, E. C. Polywka, E. Moses, J. Org. Chem., 63 (1998) 3137, for the formula (D); EP-A-1 002 801 for the formula (E); R. ter Halle, B. Colasson, E. Schulz, M. Spagnol, M. Lemaire, Tetrahedron Lett., 41 (2000) 643, for the formula (F):

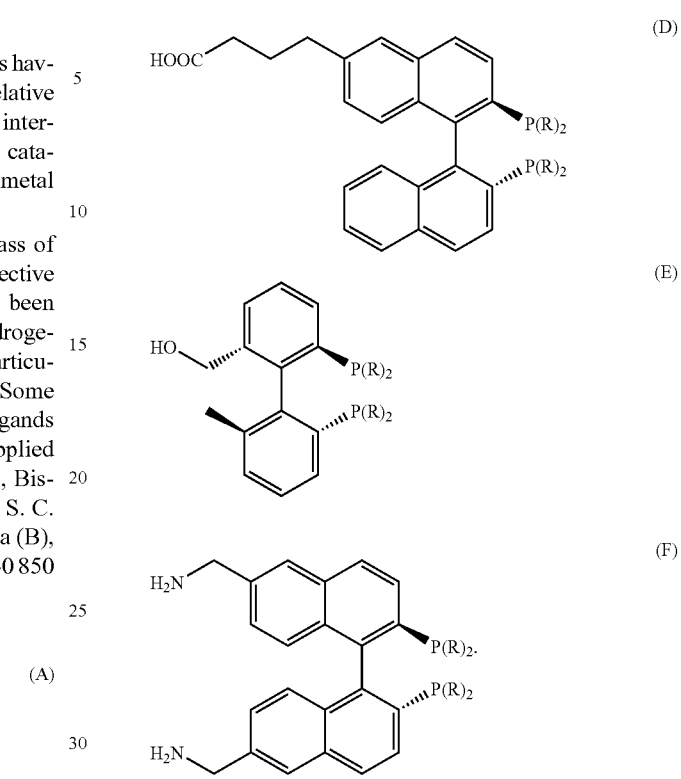

Ligands of this type can easily be covalently bound to a support or absorbed on a support by means of the functional groups —COOH, —OH or —NH$_2$, which makes them easier to be separated off and makes reuse possible. However, a disadvantage of the ligands described hitherto in the-literature is that their catalytic properties can be influenced only via the choice of the radicals bound to the phosphorus.

Although a relatively broad spectrum of ligands of the biaryldiphosphine type is already known as a result, there is still a need for improvements in respect of synthesis, catalytic properties (activity, productivity, enantioselectivity), ability for particular base structures to be finely adjusted by variation of the radicals on the base structure (tuning) or handling. Since the present-day state of knowledge does not make it possible to predict which ligand will give the best results for a given substrate without experimentation, it would be of interest in industry to have a very broad range of different ligands available in order to determine optimal ligands for a particular substrate experimentally.

Only a few chiral diphenyldiphosphines having amine groups bound directly to the benzene rings have hitherto become known, since they are difficult to synthesize. In addition, anilinic compounds are regarded as unstable since they can be decomposed oxidatively, which is regarded as troublesome both in respect of intermediates for the synthesis and in respect of the amino-substituted biphenyldisphosphines. Their catalytic properties, too, have not yet been examined. The only known compound which has been prepared hitherto (R. Schmid, M. Cereghetti, B. Heiser, P. Schönholzer, H. J. Hansen, Helv. Chim. Acta, 71 (1988) 897) is the ligand of the formula (G)

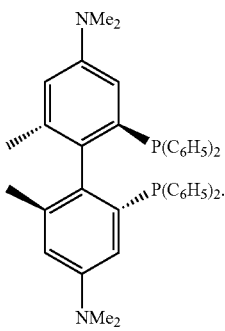

(G)

However, the electronic properties of the phosphine groups located in the catalytic center of the metal complexes can be influenced only slightly by the dimethylamine group bound in the meta positions. It is extremely desirable to have diphenyldiphosphines substituted by amine groups in which the electronic properties on the phosphorus atoms and thus the catalytic properties of the metal complexes can be influenced in a targeted manner, for example by substitution of the N atoms or by salt formation, available as ligands.

However, for the above reasons, it is not possible to foresee whether biphenyldiphosphines having an amino group in the para position relative to the phosphine can be prepared and are sufficiently stable as ligands in metal complexes in order to be able to be used in catalytic reactions.

It has now surprisingly been found that biaryldiphosphine ligands having at least one amino group in the para position relative to the phosphine group can be prepared and are sufficiently stable to be able to be used in catalysis. In addition, it has been found that the electronic properties of the ligands can be altered in a simple fashion and optimized for particular substrates with the aid of the amino group, e.g. by salt formation or by variation of the substituents on the nitrogen atom.

The present invention provides compounds of the formulae Ia and Ib,

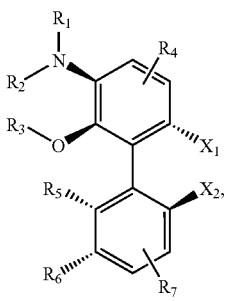

(Ia)

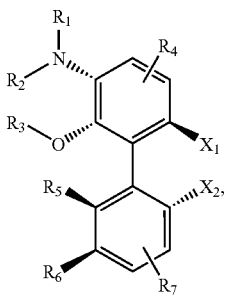

(Ib)

where
$X_1$ and $X_2$ are each, independently of one another, secondary phosphino;

$R_1$ and $R_2$ are each, independently of one another, hydrogen, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, or $R_1$ and $R_2$ together are $C_4$-$C_8$-alkylene, 3-oxapentyl-1,5-ene, —(CH$_2$)$_2$—NH—(CH$_2$)$_2$— or —(CH$_2$)$_2$—N(C$_1$-C$_4$alkyl)-(CH$_2$)$_2$—, $R_3$ is hydrogen, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, or $R_1$ is as defined above and $R_2$ and $R_3$ together are $C_2$-$C_8$-alkylidene, $C_4$-$C_8$-cycloalkylidene, $C_1$-$C_4$-alkylene, $C_2$-$C_8$-alk-1,2-enyl, —C(O)— or a group of the formula

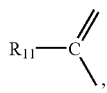

or
$R_1R_2N$ and $R_3O$ together are a group of the formula

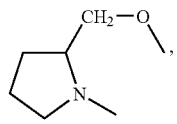

or
$R_1$, $R_3$, or $R_1$ and $R_3$ together are a protective group and $R_2$ is as defined above, $R_4$ and $R_7$ are each, independently of one another, hydrogen, $C_1$-$C_4$-alkyl, $C_1$-$C_4$-alkoxy, F, Cl or trifluoromethyl, $R_5$ is hydrogen, $R_4$ or an $R_3$O— group, where $R_3$O— groups in the two rings can be identical or different, $R_6$ is hydrogen, $R_7$ or an $R_1R_2$N— group, where $R_1R_2$N— groups in the two rings can be identical or different, $R_5$ and $R_6$ together are trimethylene, tetramethylene or —CH═CH—CH═CH—, and $R_{11}$ is $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, where $R_1$, $R_2$, $R_3$, $R_4$ and $R_7$ are unsubstituted or substituted by $C_1$-$C_4$-alkyl, $C_1$-$C_4$-alkoxy, OH, F, Cl, Br, trifluoromethyl, $C_1$-$C_4$-hydroxyalkyl, —COOH, —SO$_3$H, —C(O)O—$C_1$-$C_4$-alkyl, —SO$_3$—$C_1$-$C_4$-alkyl, —C(O)—NH$_2$, —CONHC$_1$-$C_4$-alkyl, —CON(C$_1$-$C_4$-alkyl)$_2$, —SO$_3$—NH$_2$, —SO$_2$—NHC$_1$-$C_4$-alkyl, —SO$_3$—N(C$_1$-$C_4$-alkyl)$_2$, —O$_2$C—R$_8$, —O$_3$S—R$_8$, —NH—(O)C—R$_8$, —NH—O$_3$S—R$_8$, —NH$_2$, —NHR$_9$ or —NR$_9$R$_{10}$, where R$_8$ is hydrogen, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, and R$_9$ and R$_{10}$ are each, independently of one another, $C_1$-$C_4$-alkyl, phenyl or benzyl or R$_9$ and R$_{10}$ together are tetramethylene, pentamethylene, 3-oxa-1,5-pentane or —(CH$_2$)$_2$—N(C$_1$-$C_4$-alkyl)-(CH$_2$)$_2$—.

One group of preferred substituents is $C_1$-$C_4$-alkyl, $C_1$-$C_4$-alkoxy, F, trifluoromethyl, hydroxymethyl, hydroxyethyl, —COOH, —SO$_3$H, —C(O)O-methyl or -ethyl, —SO$_3$-methyl or -ethyl, —C(O)—NH$_2$, —CONHC$_1$-$C_4$-alkyl, —CON(C$_1$-$C_4$-alkyl)$_2$, —SO$_3$—NH$_2$, —SO$_2$—NHC$_1$-$C_4$-alkyl, —SO$_3$—N(C$_1$-$C_4$-alkyl)$_2$, —O$_2$C—R$_8$, —O$_3$S—R$_8$, —NH—(O)C—R$_8$, —NH—O$_3$S—R$_8$ or —NR$_9$R$_{10}$, where R$_8$ is $C_1$-$C_4$-alkyl, $C_5$-$C_6$-cycloalkyl, $C_5$-$C_6$-cycloalkyl-$C_1$-$C_4$-alkyl, phenyl, naphthyl, benzyl or phenylethyl, and R$_9$ and $R_{10}$ are each, independently of one another, $C_1$-$C_4$-alkyl, phenyl or benzyl. Alkyl can be, for example, methyl, ethyl, n- or i-propyl and n-, i- or t-butyl.

The radicals $R_1$, $R_2$, $R_3$, $R_4$, $R_5$, $R_6$ and $R_7$ can contain chiral carbon atoms, which can prove to be particularly advantageous in the separation of the optical isomers, since diastereomers are often easier to separate by chromatography.

The individual phosphine groups $X_1$ and $X_2$ can contain monovalent hydrocarbon radicals, or the two hydrocarbon radicals together with the P atom can form a 3- to 8-membered ring. The individual phosphine groups $X_1$ and $X_2$ preferably contain two identical hydrocarbon radicals, with $X_1$ and $X_2$ being able to be different from one another. Preference is given to $X_1$ and $X_2$ being identical monovalent secondary phosphine groups. The hydrocarbon radicals can be unsubstituted or substituted and can have from 1 to 22, preferably from 1 to 12, carbon atoms. Among the compounds of the formulae I and Ia, particular preference is given to those in which the individual phosphine groups are two identical radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl or benzyl; and phenyl or benzyl substituted by halogen (for example F, Cl and Br), $C_1$-$C_6$-alkyl, $C_1$-$C_6$-haloalkyl (for example trifluoromethyl), $C_1$-$C_6$-alkoxy, $C_1$-$C_6$-haloalkoxy (for example trifluoromethoxy), $(C_6H_5)_3Si$, $(C_1$-$C_{12}$-alkyl$)_3Si$, secondary amino or $CO_2$—$C_1$-$C_6$-alkyl (for example —$CO_2CH_3$).

Examples of secondary phosphine groups in which the two hydrocarbon radicals together with the P atom form a 3- to 8-membered ring are, in particular, those of the formula

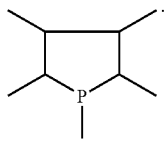

These phosphine groups are phospholanes in which the two radicals in the phosphine groups $X_1$ and $X_2$ together are, for example, unsubstituted or halogen-, $C_1$-$C_6$-alkyl- or $C_1$-$C_6$-alkoxy-substituted tetramethylene (or trimethylene or pentamethylene). The substituents are preferably located in the two ortho positions relative to the P atom, with the substituents bound to the carbon atoms being able to be hydrogen, $C_1$-$C_4$-alkyl, phenyl, benzyl, $C_1$-$C_4$-alkoxy, phenyloxy or benzyloxy. Furthermore, two adjacent substituents on carbon can also be $C_1$-$C_4$-alkylidenedioxyl.

The phosphine groups can also be groups of the formula

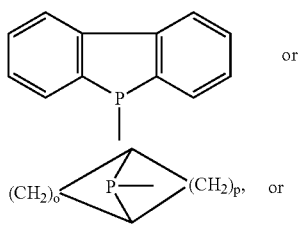

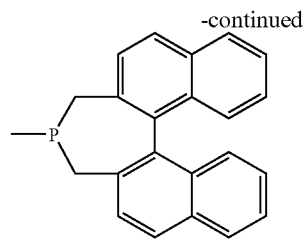

where o and p are each, independently of one another, an integer from 2 to 10 and the sum of o+p is from 4 to 12, preferably from 5 to 8, and the phenyl rings are unsubstituted or substituted by $C_1$-$C_4$-alkyl or $C_1$-$C_4$-alkoxy. Examples are [3.3.1]phobyl and [4.2.1]phobyl of the formulae

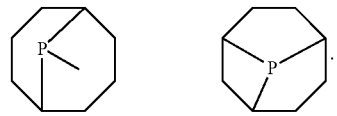

Examples of alkyl substituents on P, which preferably contain from 1 to 6 carbon atoms, are methyl, ethyl, n-propyl, i-propyl, n-butyl, i-butyl, t-butyl and the isomers of pentyl and hexyl. Examples of unsubstituted or alkyl-substituted cycloalkyl substituents on P are cyclo-pentyl, cyclohexyl, methylcyclohexyl and ethylcyclohexyl and dimethylcyclohexyl. Examples of alkyl-, alkoxy-, haloalkyl-, haloalkoxy-substituted phenyl and benzyl substituents on P are methylphenyl, dimethylphenyl, trimethylphenyl, ethylphenyl, methylbenzyl, methoxyphenyl, dimethoxyphenyl, trifluoromethylphenyl, bistrifluoromethylphenyl, tristrifluoromethylphenyl, trifluoromethoxyphenyl, bistrifluoromethoxyphenyl, dimethylaminophenyl, 3,5-di-t-butylphen-1-yl, 3,5-di-t-butyl-4-methoxyphen-1-yl, 3,5-di-t-butyl-4-dimethylaminophen-1-yl, 3,5-di-i-propylphen-1-yl, 3,5-di-i-propyl-4-methoxyphen-1-yl, 3,5-di-i-propyl4-dimethylaminophen-1-yl, 3,5-di-methyl-4-methoxyphen-1-yl, 3,5-di-methyl-4-dimethylaminophen-1-yl and 3,4,5-trimethoxyphen-1-yl.

Preferred phosphine groups are those containing identical radicals selected from the group consisting of $C_1$-$C_6$-alkyl, unsubstituted cyclopentyl or cyclohexyl or cyclopentyl or cyclohexyl substituted by from 1 to 3 $C_1$-$C_4$-alkyl or $C_1$-$C_4$-alkoxy groups, benzyl; and in particular phenyl which is unsubstituted or substituted by from 1 to 3 $C_1$-$C_4$-alkyl, $C_1$-$C_4$-alkoxy, $(C_1$-$C_4$-alkyl$)_2N$—, F, Cl, $C_1$-$C_4$-fluoroalkyl or $C_1$-$C_4$-fluoroalkoxy groups.

In the compounds of the formulae Ia and Ib, $X_1$ is preferably a —$P(R)_2$ group and $X_2$ is preferably a —$P(R')_2$ group, where R and R' are each, independently of one another, a hydrocarbon radical which has from 1 to 20 carbon atoms and is unsubstituted or substituted by halogen, $C_1$-$C_6$-alkyl, $C_1$-$C_6$-haloalkyl, $C_1$-$C_6$-alkoxy, $C_1$-$C_6$-haloalkoxy, —$CO_2$—$C_1$-$C_6$-alkyl, $(C_1$-$C_4$-alkyl$)_2N$—, $(C_6H_5)_3Si$ or $(C_1$-$C_{12}$-alkyl$)_3Si$; or the radicals R and R' together are unsubstituted or $C_1$-$C_4$-alkyl- and/or $C_1$-$C_4$-alkoxy-substituted tetramethylene or pentamethylene.

Preference is given to R and R' being identical radicals selected from the group consisting of branched $C_3$-$C_6$-alkyl, unsubstituted cyclopentyl or cyclohexyl or cyclopentyl or cyclohexyl substituted by from one to three $C_1$-$C_4$-alkyl or $C_1$-$C_4$-alkoxy groups, unsubstituted benzyl or benzyl substituted by from one to three $C_1$-$C_4$-alkyl or $C_1$-$C_4$-alkoxy groups and in particular unsubstituted phenyl or phenyl substituted by from one to three $C_1$-$C_4$-alkyl, $C_1$-$C_4$-alkoxy, —$NH_2$, ($C_1$-$C_4$-alkyl)NH—, ($C_1$-$C_4$-alkyl)$_2$N—, OH, F, Cl, $C_1$-$C_4$-fluoroalkyl or $C_1$-$C_4$-fluoroalkoxy groups.

R and $R^6$ are particularly preferably identical radicals selected from the group consisting of α-branched $C_3$-$C_6$-alkyl, unsubstituted cyclopentyl, cyclohexyl or cyclopentyl, cyclohexyl substituted by from one to three $C_1$-$C_4$-alkyl, $C_1$-$C_4$-alkoxy groups and unsubstituted phenyl or phenyl substituted by from one to three $C_1$-$C_4$-alkyl, $C_1$-$C_4$-alkoxy or $C_1$-$C_4$-fluoroalkyl groups.

$R_2$ is preferably a substituent on the N atom, for example $C_1$-$C_4$-alkyl, $C_5$-$C_6$-cycloalkyl, $C_5$-$C_6$-cycloalkyl-$C_1$-$C_2$-alkyl, phenyl or benzyl. $R_1$ and $R_2$ together are preferably $C_4$-$C_5$-alkylene, 3-oxapentyl-1,5-ene or —($CH_2$)$_2$—N(methyl)-($CH_2$)$_2$—. $R_1$ is preferably a hydrogen atom or has one of the preferred meanings of $R_2$, with $R_1$ and $R_2$ being able to be identical or different. Some examples are methyl, ethyl, propyl, n-butyl, cyclopentyl, cyclohexyl, cyclohexylmethyl, tetramethylene, pentamethylene, phenyl and benzyl.

$R_3$ is preferably a substituent on the O atom, for example $C_1$-$C_4$-alkyl, $C_5$-$C_6$-cycloalkyl, $C_5$-$C_6$-cycloalkyl-$C_1$-$C_2$-alkyl, phenyl or benzyl. Some examples are methyl, ethyl, n- and i-propyl, n-, i- and t-butyl, cyclopentyl, cyclohexyl and cyclohexylmethyl.

$R_1$ is preferably a substituent on the N atom and $R_2$ and $R_3$ are preferably together $C_2$-$C_4$-alkylidene, $C_5$-$C_6$-cycloalkylidene, $C_1$-$C_2$-alkylene, $C_2$-$C_4$-alk-1,2-enyl, —C(O)— or a group of the formula

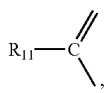

where $R_{11}$ is preferably $C_1$-$C_4$-alkyl, $C_5$-$C_6$-cycloalkyl, $C_5$-$C_6$-cycloalkylmethyl, phenyl or benzyl.

Some examples of $R_2$ and $R_3$ together are ethylidene, propylidene, butylidene, cyclohexylidene, benzylidene, methylene, 1,2-ethylene, 1,2-propylene, 1,2-ethenylene, 1,2-propenylene and 1,2-butenylene.

Some examples of $R_{11}$ are methyl, ethyl, n- and i-propyl, n-, i- and t-butyl, cyclopentyl, cyclohexyl, cyclohexylmethyl, phenyl and benzyl.

Suitable protective groups $R_1$ and $R_3$ are, for example, radicals which form an ether bond, an ester bond, an amide bond, a carbonate bond, a carbamate bond or a urethane bond, which can easily be cleaved again either hydrolytically or hydrogenolytically. Suitable protective groups can be radicals of the formula

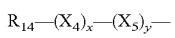

where $R_{14}$ is an aliphatic, cycloaliphatic, aromatic or araliphatic radical having from 1 to 8 carbon atoms, $X_4$ is —O—, —NH— or —N($C_1$-$C_4$-alkyl), $X_5$ is —C(O)— or —$SO_2$—, and x and y are 0, or x is 0 or 1 and y is 1. When $R_1$ and $R_3$ form a protective group, this can be, for example, —C(O)—. Further examples of protective groups are acetate, trichloroactetate, triflate, methylsulfonate, tosylate, benzyl, diphenylmethyl, trityl, trimethylsilyl, methoxycarbonyl and methylaminocarbonyl.

$R_4$ and $R_7$ are preferably each hydrogen. When $R_4$ and $R_7$ are substituents, these are preferably $C_1$-$C_2$-alkyl, $C_1$-$C_2$-alkoxy, F, Cl or trifluoromethyl.

For the purposes of the invention, preference is given to compounds which are symmetrical and in which $X_1$ and $X_2$ in the formulae Ia and Ib are identical and $R_5$ is an $R_3$O— group and $R_6$ is an $R_1R_2$N— group.

In a preferred embodiment, the biphenyldiphosphines of the invention correspond to the formula Ic,

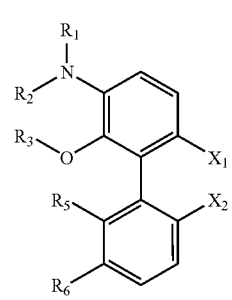

(Ic)

where $R_1$ is hydrogen and $R_2$ and $R_3$ are each, independently of one another, $C_1$-$C_4$-alkyl, preferably methyl or ethyl, or $R_1$, $R_2$ and $R_3$ are each, independently of one another $C_1$-$C_4$-alkyl, preferably methyl or ethyl, $R_5$ is hydrogen or an $OR_3$ group, $R_6$ is hydrogen or an $NR_1R_2$ group, or $R_5$ and $R_6$ together are —CH=CH—CH=CH—, and $X_1$ and $X_2$ are each secondary phosphino. The abovementioned embodiments and preferences apply to $X_1$ and $X_2$.

In another preferred embodiment, the biphenyldiphosphines of the invention correspond to the formula Id,

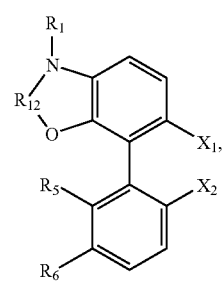

(Id)

where $R_1$ is hydrogen and $R_2$ and $R_3$ are each, independently of one another, $C_1$-$C_4$-alkyl, preferably methyl or ethyl, or $R_1$, $R_2$ and $R_3$ are each, independently of one another, $C_1$-$C_4$-alkyl, preferably methyl or ethyl, $R_5$ and $R_6$ are each hydrogen or $R_5$ and $R_6$ together are an —$NR_1$—$R_{12}$—O— group, $X_1$ and $X_2$ are each secondary phosphino, and $R_{12}$ is 1,2-ethylene, 1,2-ethenylene, —C(O)— or a group of the formula

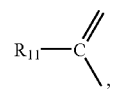

where $R_{11}$ is branched $C_3$-$C_8$-alkyl, $C_5$-$C_6$-cycloalkyl, phenyl or benzyl. The abovementioned embodiments and preferences apply to $X_1$ and $X_2$.

Some preferred specific compounds according to the invention correspond to the formulae Ie, If, Ig, Ih and Ii,

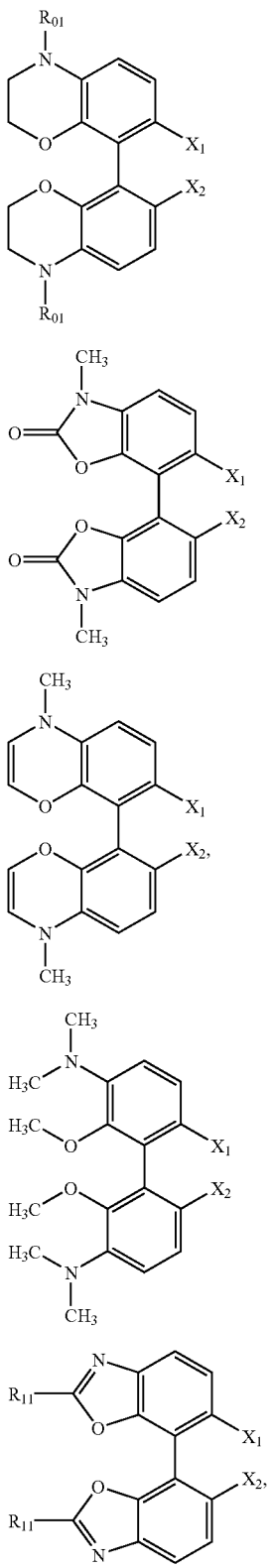

where $R_{01}$ is hydrogen, $C_1$-$C_8$-alkyl, $C_5$-$C_6$-cycloalkyl, phenyl or benzyl, $R_{11}$ is phenyl or t-butyl, and $X_1$ and $X_2$ are as defined above, including the preferences. Preferred groups $X_1$ and $X_2$ are diphenylphosphino, ditoluylphosphino, dixylylphosphino, di(methoxyphenyl)phosphino, di(trifluoromethylphenyl)phosphino, dicyclohexylphosphino, difurylphosphino, di(4-methoxy-3,5-dimethylphenyl) phosphino, di[(3,5-bistrifluoromethyl)phenyl]phosphino and di-t-butylphosphino.

The compounds of the formula I can be prepared by methods which are known per se (Segphos synthesis) and are described in the references mentioned at the outset. Further details on the method of preparation may be found in:

[1] R. Schmid, E. A. Broger, M. Cereghetti, Y. Crameri, J. Foricher, M. Lalonde, R. K. Müller, M. Scalone, G. Schoettel and U. Zutter, Pure & Appl. Chem., 68 (199) 131-388.

[2] EP 0 926 152 A1

[3] H. Geissler in Transition Metals for Organic Synthesis (Eds.: M. Beller, C. Bolm), Wiley-VCH, Weinheim, 1998, 158-183, and in the references mentioned in the publications.

In a first method, it is possible to start out from, for example, compounds of the formula II

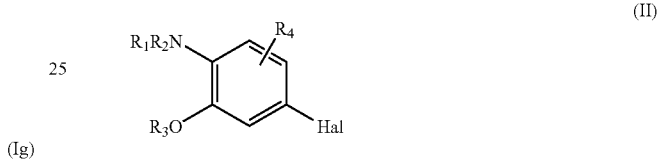

where $R_1$, $R_2$ and $R_3$ are as defined above, and react these firstly with a Grignard metal such as magnesium or lithium alkyl and then with a phosphine oxide of the formula RRP(O)-Hal or a phosphate halide of the formula $(R°O)_2P(O)$-Hal, where Hal is Cl, Br or I, R° is, for example, $C_1$-$C_6$-alkyl (methyl, ethyl) or phenyl and R is as defined above. Compounds of the formula II can also be reacted directly with $(R°O)_2P(O)$-Hal using Pd-catalyzed methods. Two equivalents of the resulting compound of the formula III for preparing symmetrical compounds,

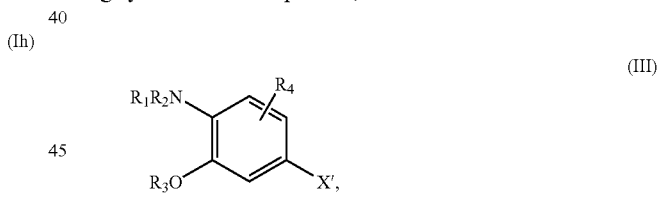

where X' is RRP(O)— or $(R°O)_2P(O)$—, or one equivalent of a compound of the formula III and one equivalent of a compound of the formula IV which can be prepared as described in the first process step and in which $R_5$, $R_6$ and X' are as defined above, X' in the formula IV can be different from X' in the formula III,

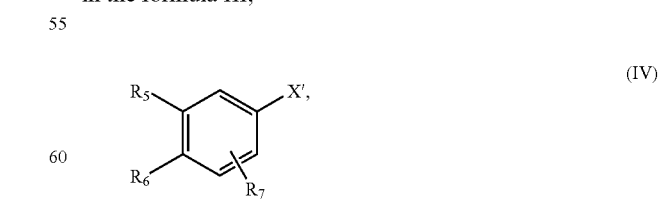

are firstly metalated in the ortho position relative to the group X', for example by means of lithium amides, and then reacted in the presence of a metal salt such as $CuCl_2$ or $FeCl_3$ to form compounds of the formula V

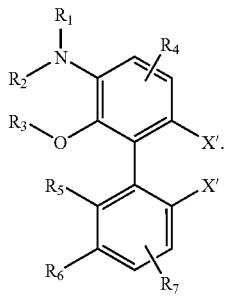

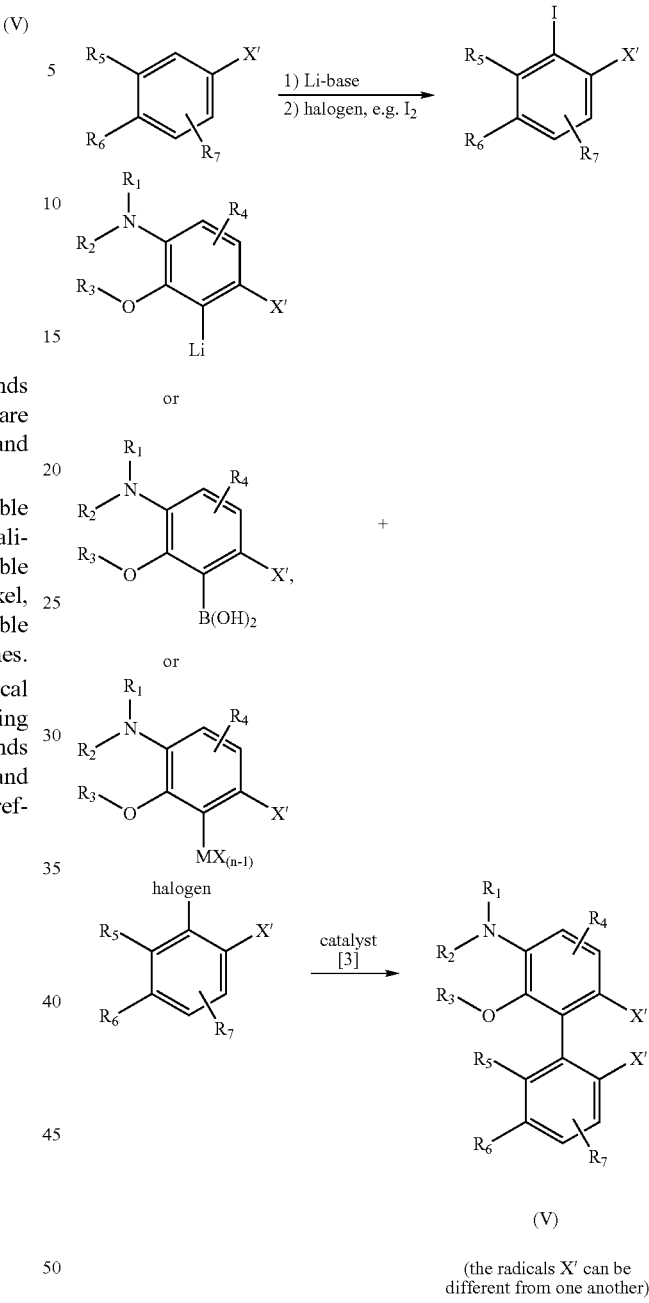

This synthesis also makes it possible to obtain compounds of the formulae Ia and Ib in which the groups $X_1$ and $X_2$ are different (R is different from R' in the groups —$PR_2$ and $PR'_2$).

The reactions are advantageously carried out in suitable inert solvents such as ethers, nitriles, carboxamides or aliphatic, cycloaliphatic or aromatic hydrocarbons. Suitable metal salts are, for example, halides of iron, cobalt and nickel, in particular iron(ill) chloride and iron(III) bromide. Suitable bases are, for example, open-chain or cyclic, tertiary amines.

The preparation of both symmetrical and unsymmetrical compounds can also be carried out using catalytic coupling methods as described in [3]. For this purpose, the compounds of the formulae III and IV are metalated or halogenated and subsequently coupled using catalytic methods, with $R_5$ preferably being hydrogen:

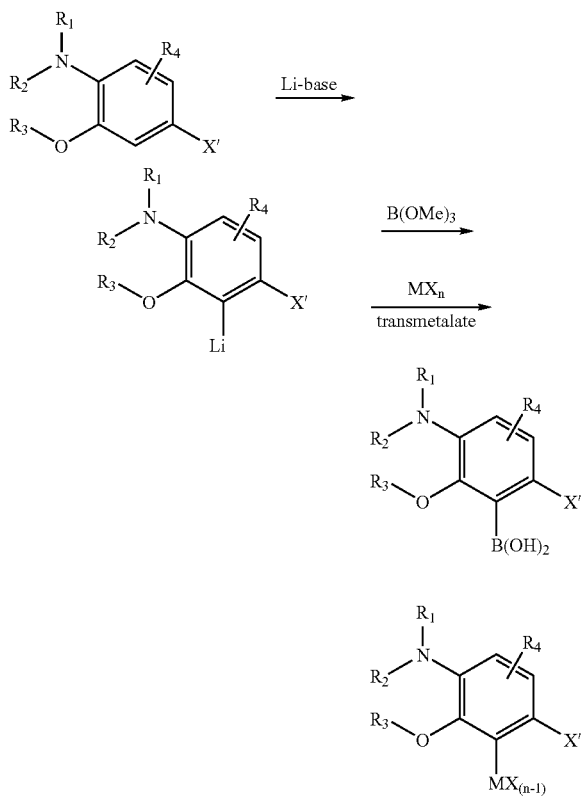

(the radicals X' can be different from one another)

The compounds of the formula V can then be converted into the compounds according to the invention of the formula I in a manner known per se by means of reduction of the phosphine oxide group. As hydrogenating agents, it is possible to use metal hydrides, for example LiH, NaH, KH or Li(AlH$_4$). It is more advantageous to use alkylsilanes or chlorosilanes and alkylstannanes or chlorostannanes, for example trichlorosilane or trichlorostannane.

If $R_1$ to $R_7$ in the phosphine oxides of the formula V are not chiral radicals, the preparation generally gives racemates from which the desired enantiomers can be isolated by resolution by means of crystallization using a chiral auxiliary reagent or by chromatographic methods, with resolution advantageously being carried out using the compounds of the formula V. If a radical $R_1$ to $R_7$ is optically active, the optical resolution is often easier, since diastereomers can be separated more easily by chromatography, even on a preparative scale.

Phosphonate compounds V having nonchiral radical $R_1$-$R_7$ can be separated into their enantiomers by means of crystallization using a chiral auxiliary reagent or chromatographic methods in a manner similar to the phosphine oxide compounds V. The optically pure or optically enriched phosphonate compounds are subsequently converted into the desired phosphine oxides by known methods [1] by means of reaction with Grignard reagents R—Mg—X and finally reduced as described above to give compounds of the formulae Ia and Ib.

The novel compounds of the formulae Ia and Ib can, in a second method, also be prepared by a novel process in which halogenation and introduction of the phosphine group into the biphenyl skeleton is carried out. Surprisingly, the halogenation proceeds so regioselectively that high yields can be achieved.

The invention further provides a process for preparing compounds of the formulae Ia and Ib,

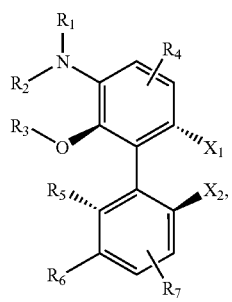

(Ia)

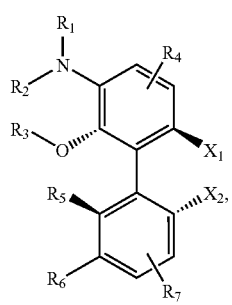

(Ib)

where $R_1$, $R_2$, $R_3$, $R_4$, $R_5$, $R_6$, $R_7$, $X_1$ and $X_2$ are as defined above, which comprises the steps:

a) halogenation of a compound of the formula VI

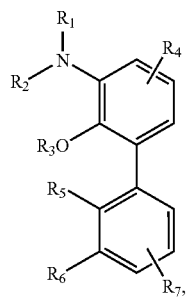

(VI)

where $R_1$, $R_2$, $R_3$, $R_4$, $R_5$, $R_6$ and $R_7$ are as defined above, or $R_1$ is a protective group which can be split off and $R_2$ is hydrogen or is as defined above, or $R_3$ is a protective group which can be split off, or $R_1$ and $R_3$ form a protective group which can be split off and $R_2$ is hydrogen or is as defined above, by means of chlorine, bromine or iodine to form a compound of the formula VII

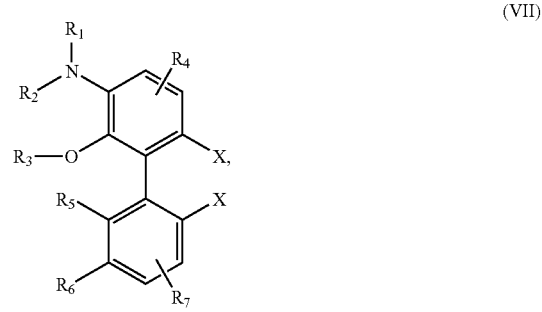

(VII)

where X is chlorine, bromine or iodine, b) if appropriate to introduce the radicals $R_2$ and $R_3$, removal of the protective groups to form OH-functional and NH-functional groups and replacement of the H atoms in the OH-functional and NH-functional groups by means of a reagent $R_2$—$Y_2$, $R_3$—$Y_2$ or $Y_2$—$R_{13}$—$Y_2$, where $Y_2$ is a leaving group and $R_{13}$ is 1,2-alkylene or 1,2-cycloalkylene, to produce compounds of the formula VII, and if appropriate resolution of the racemates of the formula VII (by known methods such as crystallization using a chiral auxiliary reagent or chromatographic methods using chiral columns. Compounds of the formula VII in which at least one of the radicals $R_1$ to $R_7$ is optically active are particularly advantageous for the preparation of optically pure ligands. In these cases, mixtures of diastereomers which can be separated by methods known per se, e.g. chromatography or crystallization, are obtained. The optically active radicals can, if necessary, be used as auxiliary or protective groups and can subsequently be replaced by other radicals) to give the enantiomers of the formulae VIIa and VIIb

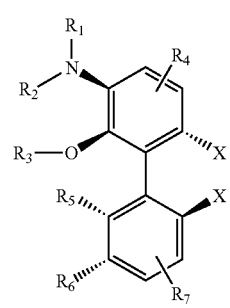

VIIa

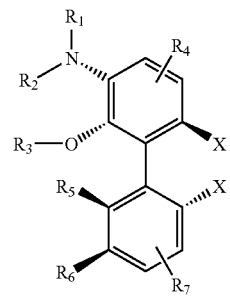

VIIb c) metalation of the compounds of the formula VII, VIIa or VIIb, for example by means of a lithium alkyl, and subsequent reaction with a halophosphine of the formula $X_3$—PRR ($X_3$ is halogen) to give diphosphines of the formula VIII, Ia or Ib, or with a halophosphine oxide of the formula $X_3$—P(O)RR to give diphosphine oxides of the formula IX, IXa or IXb, or with a phosphonate of the formula $X_3$—P(O)(OR°)$_2$ to give phosphonates of the formula X, Xa or Xb:

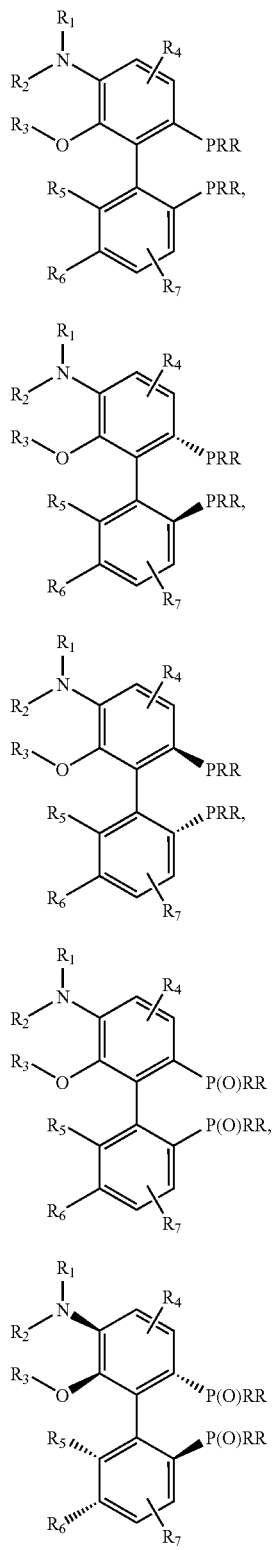

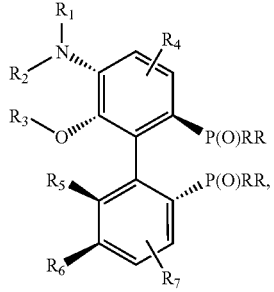

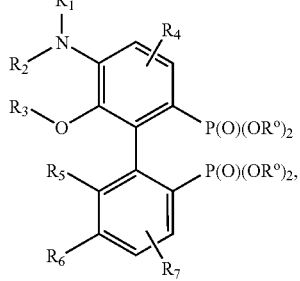

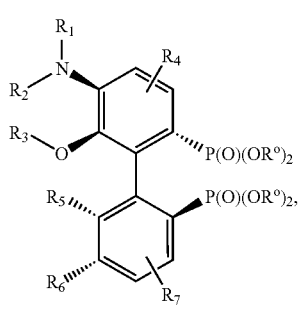

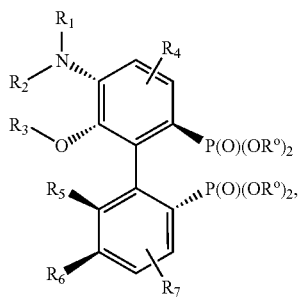

where R is a radical forming $X_1/X_2$, for example a hydrocarbon radical having from 1 to 20 carbon atoms and R° is $C_1$-$C_6$-alkyl or phenyl, d) oxidation of the phosphine groups in compounds of the formula VIII, VIIIa or VIIIb by means of an oxidant to form compounds of the formula IX, IXa or IXb, e) if a racemic starting material of the formula VII is used, resolution of the racemates of the formula VIII to give the enantiomers Ia and Ib, or resolution of the racemates of the formula IX to give the enantiomers of the formulae IXa and IXb, or resolution of the racemates of the formula X to give the enantiomers of the formulae Xa and Xb, and reaction of compounds of the formulae Xa and Xb with R—Mg—X to form phosphine oxides of the formula IXa and IXb, and f) reduction of the phosphine oxide group in the compounds of the formulae IXa and IXb to produce compounds of the formulae Ia and Ib.

The compounds of the formula VI can be prepared as follows. Commercially available 2,2'-dihydroxy-3,3'-dinitro-5,5'-dichlorobiphenyl (Niclofan) can be catalytically hydrogenated in a manner known per se by means of hydrogen and in the presence of hydrogenation catalysts, for example palladium or platinum, to form 2,2'-dihydroxy-3,3'-diaminobiphenyl (1). The H atoms of the hydroxy groups and one H atom of the amino group can be replaced by protective groups and the second H atom of the amino group can then be replaced by a radical $R_2$. The resulting compounds of the formula VI can be used in process step a).

As an alternative, the H atoms of the hydroxy groups and the H atoms of the amino group in the compounds (1) can be replaced by radicals $R_1$, $R_2$ and $R_3$ in a manner known per se. The resulting compounds of the formula VI can be used in process step a).

Methods and reagents for substituting OH and $NH_2$ groups are prior art and are illustrated in the examples. The introduction and removal of protective groups and methods and reagents for this purpose are also prior art and will not be described in more detail here. Suitable protective groups are, for example, radicals which form an ether bond, an ester bond, an amide bond, a carbonate bond, a carbamate bond or a urethane bond, which can easily be dissociated again either hydrolytically or hydrogenolytically. Suitable radicals of proteitive groups can correspond to the formula

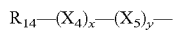

where $R_{14}$ is an aliphatic, cycloaliphatic, aromatic or araliphatic radical having from 1 to 8 carbon atoms, $X_4$ is —O—, —NH— or —N($C_1$-$C_4$-alkyl), $X_5$ is —C(O)— or —$SO_2$— and x is 0 or 1 and y is 1 or x and y are each 0 when $X_4$ is O. If $R_1$ and $R_3$ form a protective group, this can be, for example, —C(O)—. Further examples of protective groups are acetate, trichloroacetate, triflate, methylsulfonate, tosylate, benzyl, diphenylmethyl, trityl, trimethylsilyl, methoxycarbonyl and methylaminocarbonyl. It should be pointed out that protective groups can at the same time be radicals $R_1$, $R_2$ and $R_3$ and are only replaced when other radicals $R_1$, $R_2$, and $R_3$ are to be introduced.

A particularly advantageous process for preparing selected cyclic compounds of the formulae Ia and Ib starts out from compounds of the formula

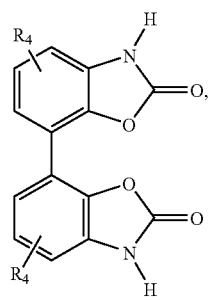

which can be reacted with 1,2-dihaloethane, for example 1,2-dibromoethane, in the presence of alkali metal bases, to form compounds of the formula

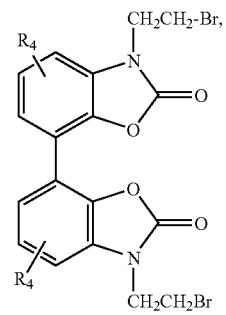

which can firstly be halogenated, for example by means of bromine, to form compounds of the formula

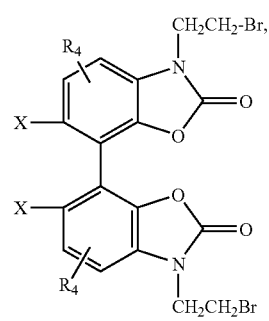

which can be cyclized in the presence of alkali metal hydroxides to form compounds of the formula A:

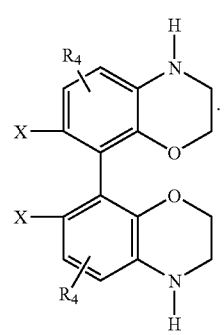

(A)

The compounds A are a central intermediate for the preparation of enantiomerically pure diphenyldiphosphines having a fused-on N,O-heterocyclic six-membered ring. Here, it has been found to be advantageous to carry out the separation of the optical isomers at the stage of the compounds of the formula A. It has been found that the chromatographic separation on chiral columns proceeds particularly well when the H atoms of the NH groups have been replaced by chiral radicals. Carboxylic acids or esters thereof or halides thereof which have a chiral C atom in the α or β position and can readily be split off again by hydrolysis have been found to be particularly useful for this purpose. Preferred carboxylic acids and derivatives are α and β aminocarboxylic acids, in particular cyclic aminocarboxylic acids such as proline. After the optical resolution, the auxiliary groups are split off again to give optical isomers of the formulae A1 and A2,

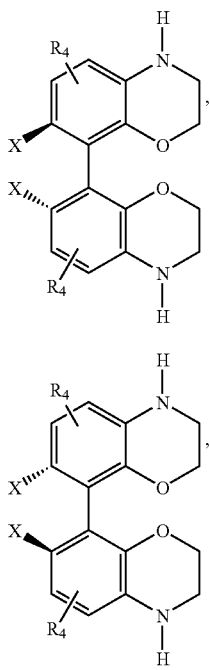

(A1)

(A2)

in which, if desired, the H atoms can be replaced by $R_1$ groups in a manner known per se to form compounds of the formulae B1 and B2:

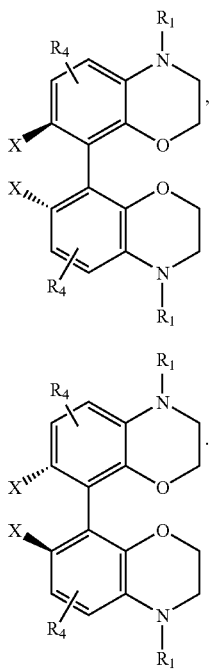

(B1)

(B2)

The compounds of the formulae B1 and B2 can then be reacted with lithium and then with halophosphines to give particularly preferred diphosphines according to the invention having the formulae Ij and Ik

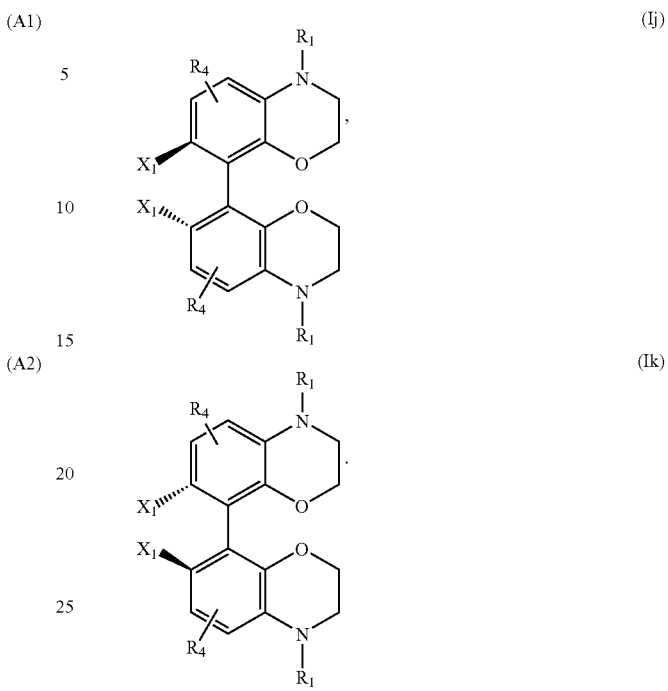

(Ij)

(Ik)

An auxiliary reagent which acts as reaction accelerator, for example hexamethylphosphoramide, can be added both before introduction of phosphine groups and in process step c) to avoid or suppress possible racemization during the reaction with lithium alkyl.

The reactions of process steps a) to d) and f) can be carried out without solvent or in inert solvents, with one solvent or mixtures of solvents being able to be used. Suitable solvents are, for example, aliphatic, cycloaliphatic and aromatic hydrocarbons (pentane, hexane, heptane, petroleum ether, cyclohexane, methylcyclohexane, benzene, toluene, xylene), aliphatic halogenated hydrocarbons (methylene chloride, chloroform, dichloroethane and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethylformamide), acyclic ureas (dimethylimidazoline), sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether), nitromethane and water. Reactions with lithium alkyl are mainly carried out in alphatic or aromatic hydrocarbons or ethers.

The reactions of process steps a) to d) and f) can be carried out with cooling or heating, for example in a range from −100° C. to 200° C., preferably from −60 to 150° C. The temperatures to be employed in the individual reactions are known to those skilled in the art and can also be taken from the examples.

The halogenation of process step a) is advantageously carried out in the presence of Lewis acids, for example metal halides such as FeCl$_3$ or FeBr$_3$, which can also be generated in situ.

The hydrolytic removal (process step b) of protective groups in a basic or acid reaction medium is known. In general, alkali metal hydroxides such as NaOH or KOH and mineral acids such as hydrochloric acid or sulfuric acid are used. The hydrogenolytic removal is generally carried out using hydrogen in the presence of noble metals such as platinum or palladium as catalysts. The haloaminobisphenols obtained are not very stable and are advantageously not isolated but used directly in the subsequent reactions for reaction with reagents R$_1$—Y$_2$, R$_2$—Y$_2$, R$_3$—Y$_2$ or Y$_2$—R$_{13}$—Y$_2$. The reagents are reagents for introducing alkyl, cycloalkyl, cycloalkylalkyl and aralkyl groups. Leaving groups in such reagents are known. Y$_2$ is mostly halogen such as chlorine, bromine or iodine, or an acid radical such as sulfonate or sulfate. Cyclic sulfates and carbonates having a radical R$_{13}$ are also suitable.

Racemic compounds can be separated into their enantiomers by means of, for example, preparative chromatographic methods (for example HPLC) using chiral stationary phases. The introduction of secondary phosphine groups to produce chiral diphosphine ligands for enantioselective catalysts according to process c) has been known for a relatively long time. As lithium alkyl, preference is given to using commercially available methyllithium or butyllithium. Process step c) gives ready-to-use diphosphine ligands, although these still have to be separated into the desired enantiomers if the resolution of the racemate has not previously been carried out at an earlier stage.

If it is simpler to carry out the resolution of the racemate via the phosphine oxides, the phosphine groups are oxidized according to process step d), because the phosphine oxides are often considerably easier to separate into the enantiomers. Suitable oxidants are air, alkali metal peroxides and, in particular, hydrogen peroxide.

The resolution of the racemate at the stage of phosphonates has the advantage that various radicals can subsequently be introduced on the phosphorus virtually without racemization. The resolution of the racemate at the phosphonate stage by crystallization with suitable chiral auxiliary reagents is known. The conversion of phosphonates into phosphine oxides has likewise been described in the literature [1].

The resolution of the racemate according to process step e) can be carried out by known methods by means of crystallization in the presence of chiral complexing agents such as dibenzoyltartaric acid. Preparative separation by means of chromatographic methods (for example HPLC) using chiral stationary phases is also advantageous. Such columns having different chiral stationary phases are commercially available.

The reduction according to process step f) can be carried out using metal hydrides such as LiH, NaH, Li(AlH$_4$), or by means of hydrosilanes or hydrostannanes, if appropriate under superatmospheric pressure. In the preferred reduction using hydrosilanes, for example trichlorosilane, it is advantageous to add tertiary amines, for example trimethylamine or triethylamine. Up to equimolar amounts of these, based on the silane, can be used here.

The compounds of the formula (racemates) and the formulae Ia and Ib (enantiomers) are obtained in high yields and high purity by the process of the invention.

Intermediates formed in the process of the invention are novel. The invention also provides compounds of the formula VII as diastereomers, a mixture of diastereomers, pure diastereomers or enantiomers in optically enriched or optically pure form,

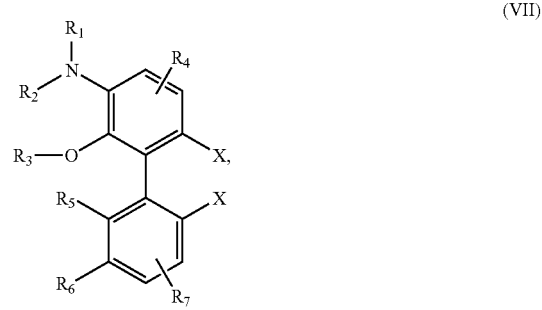

(VII)

where R$_1$, R$_2$, R$_3$, R$_4$, R$_5$, R$_6$, R$_7$ and X are as defined above, or R$_1$ or R$_2$ is a protective group which can be split off or R$_2$ and R$_3$ together form a protective group which can be split off and R$_1$, R$_3$, R$_4$, R$_5$, R$_6$, R$_7$ and X or R$_1$, R$_4$, R$_5$, R$_6$, R$_7$ and X are as defined above, and X is chlorine, bromine or iodine.

The preferred embodiments indicated for the compounds of the formulae Ia and Ib also apply to the compounds of the formulae VII.

Particularly preferred compounds of the formula VII are those of the formula VIIc (racemate), VIId or VIIe (mixtures of diastereomers, pure diastereomers, or enantiomers in optically enriched or optically pure form),

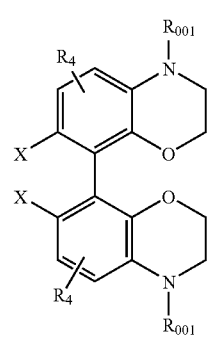

(VIIc)

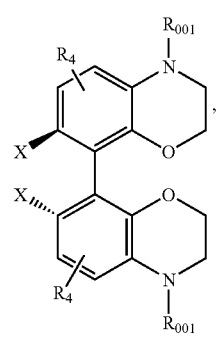

(VIId)

-continued

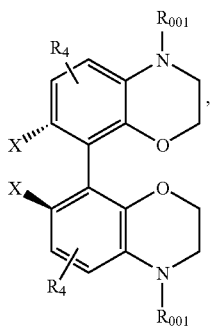

(VIIe)

where R$_{001}$ is a radical R$_1$ or a chiral auxiliary group, and X and R$_4$ are as defined above, including the preferences. As chiral auxiliary groups, preference is given to carbamide radicals of β- and in particular α-aminocarboxylic acids, very particularly preferably of proline.

Particularly preferred intermediates also include those of the formula VIIf, as racemate, as a mixture of diastereomers, pure diastereomers or enantiomers in optically enriched or optically pure form,

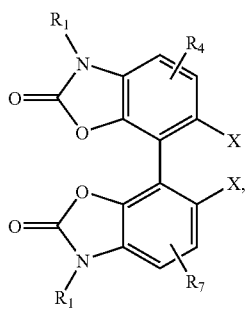

(VIIf)

where X is chlorine, bromine or iodine and R$_1$, R$_4$ and R$_7$ have the meanings indicated for compounds of the formulae Ia and Ib, including the preferences.

The invention also further provides the preproducts of the formula IX (racemates) and the formulae IXa, IXb (mixtures of diastereomers, pure diastereomers, or enantiomers in optically enriched or optically pure form),

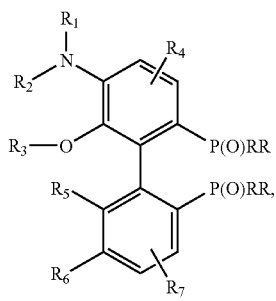

(IX)

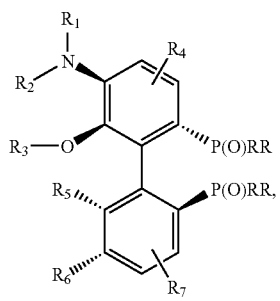

(IXa)

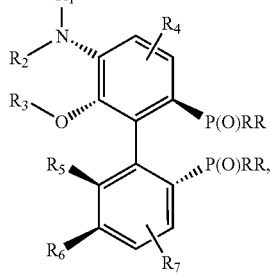

(IXb)

and the preproducts of the formula X (racemates), compounds of the formulae Xa and Xb (mixtures of diastereomers pure diastereomers, or enantiomers in optically enriched or optically pure form),

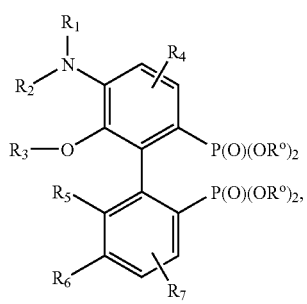

(X)

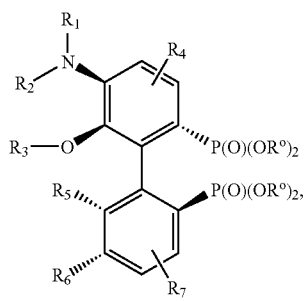

(Xa)

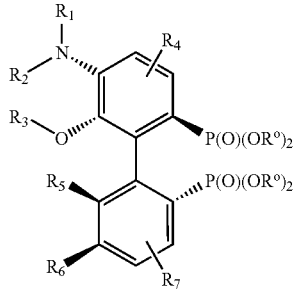

(Xb)

where $R_1$, $R_2$, $R_3$, $R_4$, $R_5$, $R_6$, $R_7$ have the meanings indicated for the compounds of the formulae I and Ia, including the preferences, $R°$ is $C_1$-$C_6$-alkyl or phenyl and R is an $X_1/X_2$-forming radical, for example a hydrocarbon radical having from 1 to 20 carbon atoms.

Particular preference is given to compounds of the formulae IX, IXa, IXb, X, Xa and Xb, in which $R_1$ is methyl, $R_2$ and $R_3$ together are 1,2-ethylene and $R_4$, $R_5$, $R_6$, $R_7$ and R have the meanings indicated for compounds of the formulae I and Ia, including the preferences, and $R°$ is $C_1$-$C_6$-alkyl or phenyl and R is an $X_1/X_2$-forming radical, for example a hydrocarbon radical having from 1 to 20 carbon atoms.

Possible methods of preparation are shown below for illustrative purposes as reaction schemes. Compounds of the formulae VII, Ia and Ib in which $R_1R_2N$ and $R_3O$ together are the group of the formula

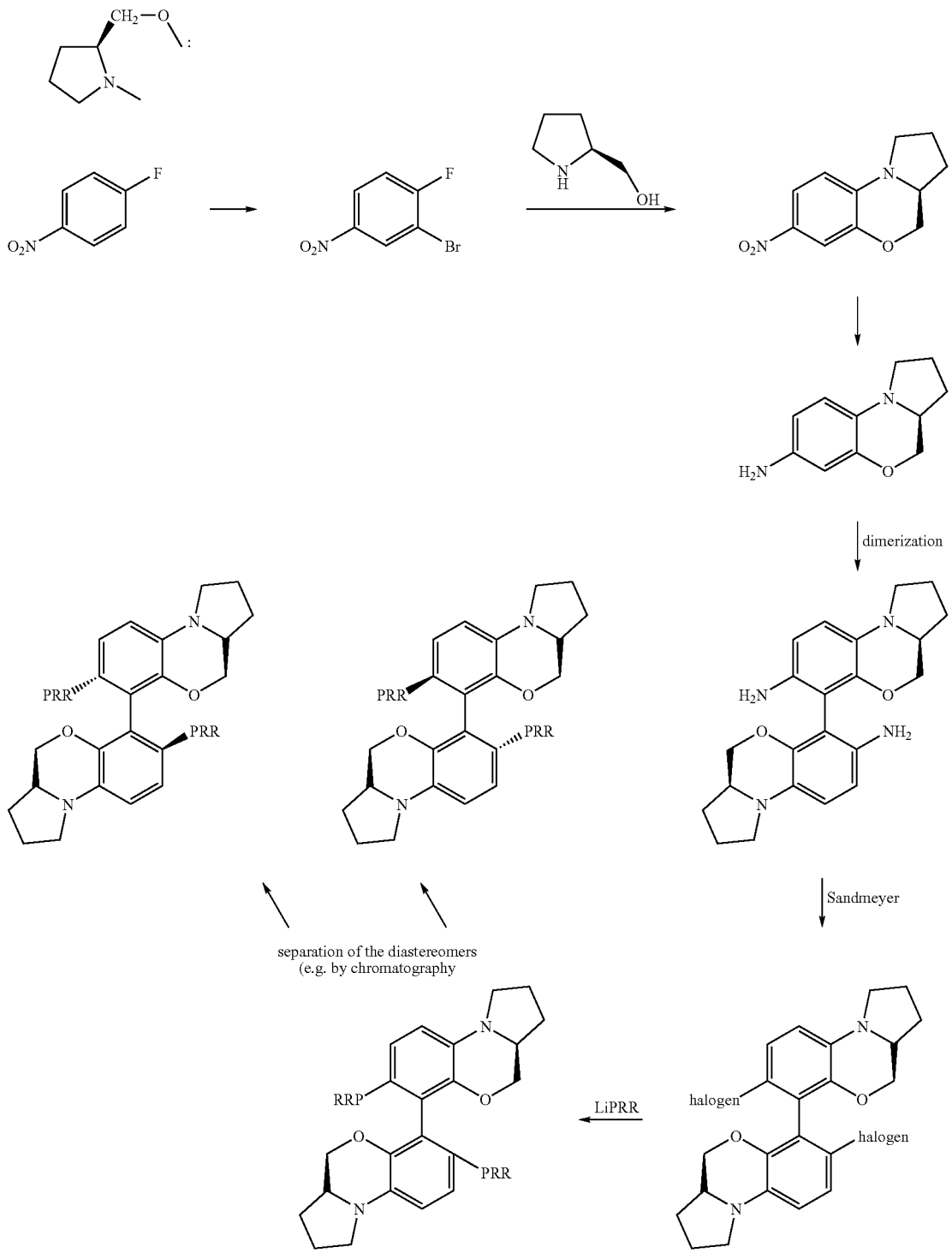

Preparation of Symmetrical Compounds (Route 1 Via Coupling):
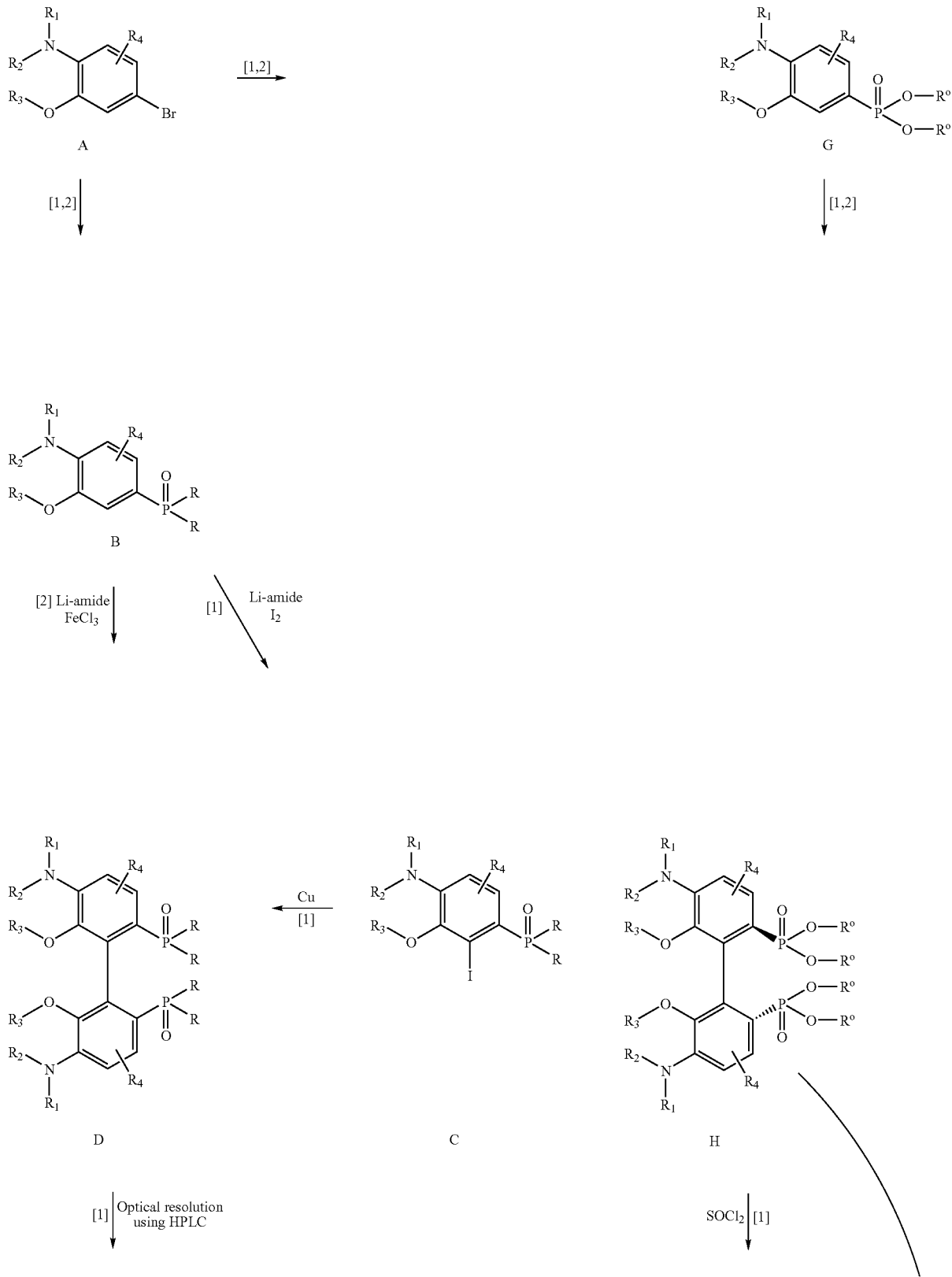

-continued
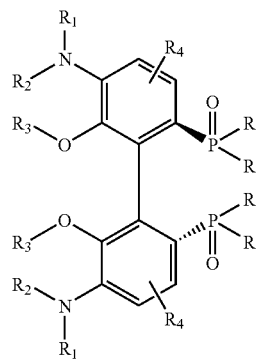
E
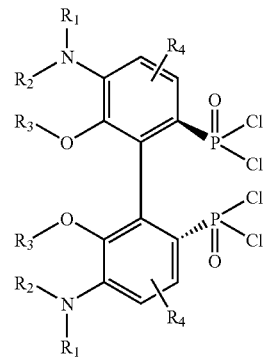
I
[1] Reduction HSiCl₃/NBu₃
R—Mg—X [1,2]
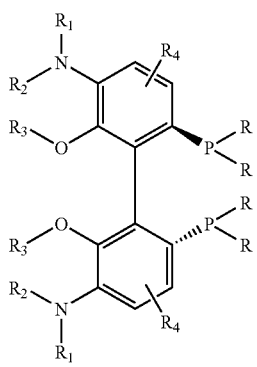
F
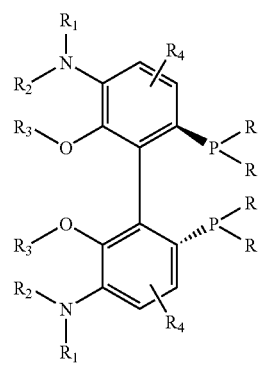
L
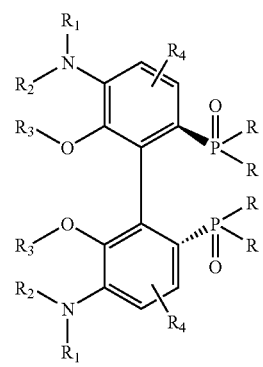
K
Reduction HSiCl₃/NBu₃ [1]
Rg can be, for example, $C_1$–$C_4$-alkyl or phenyl.
Route 2, Via Preformed Biaryl:
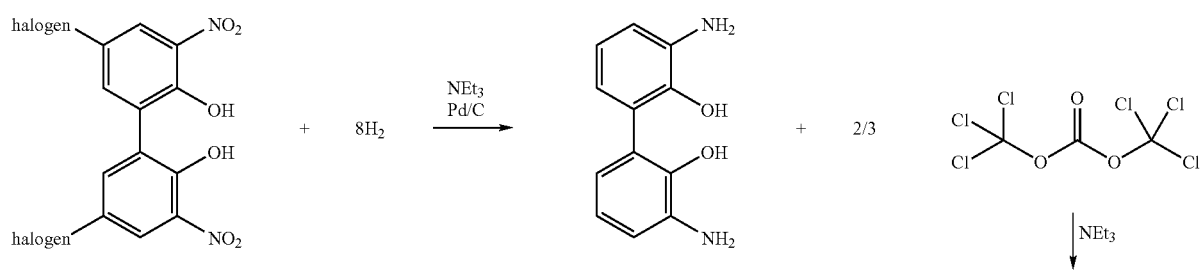
NEt₃ Pd/C
NEt₃

31
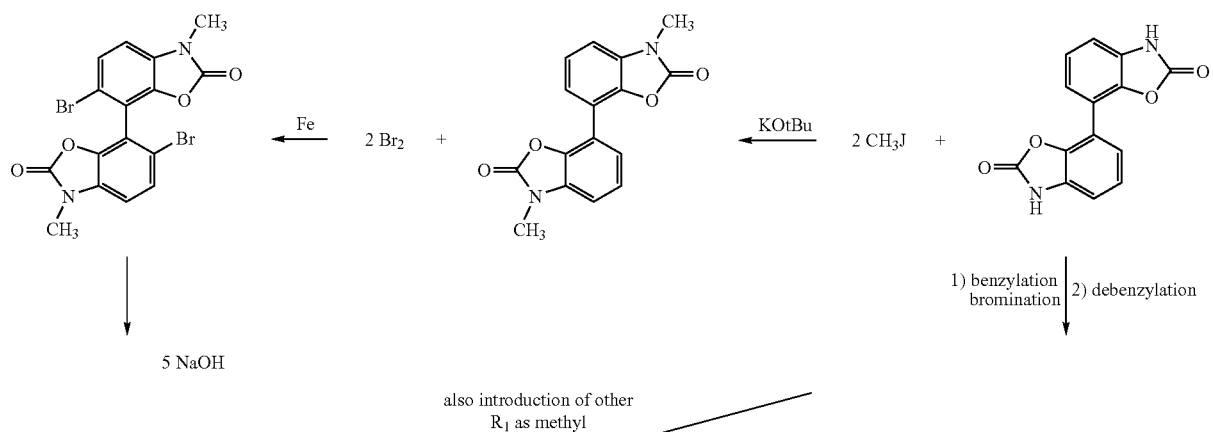
-continued
32
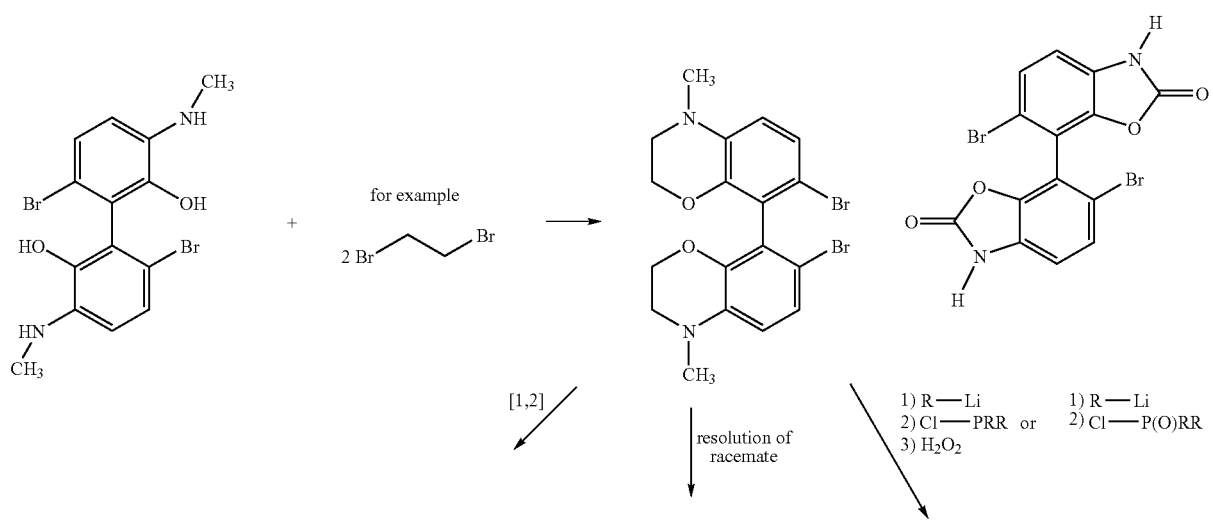
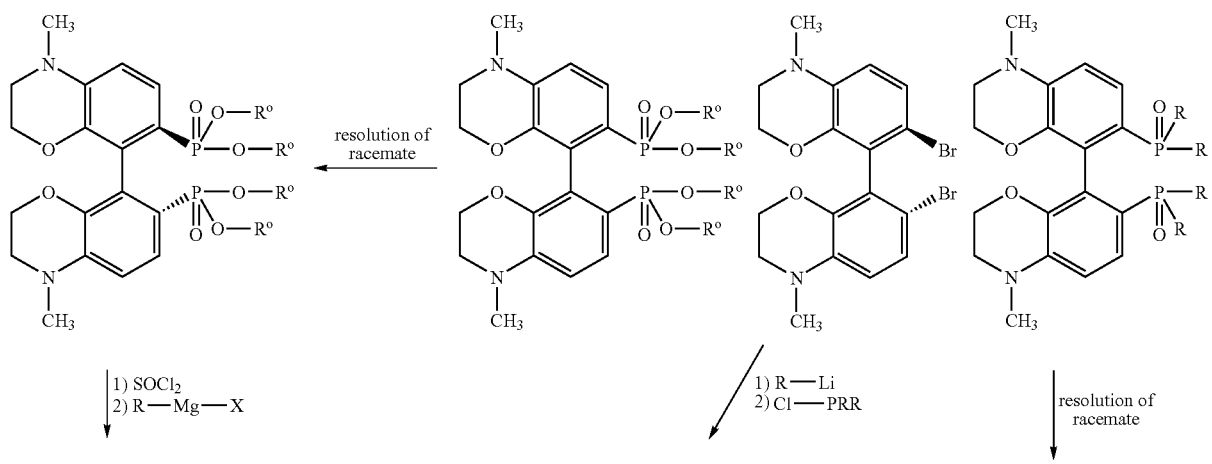

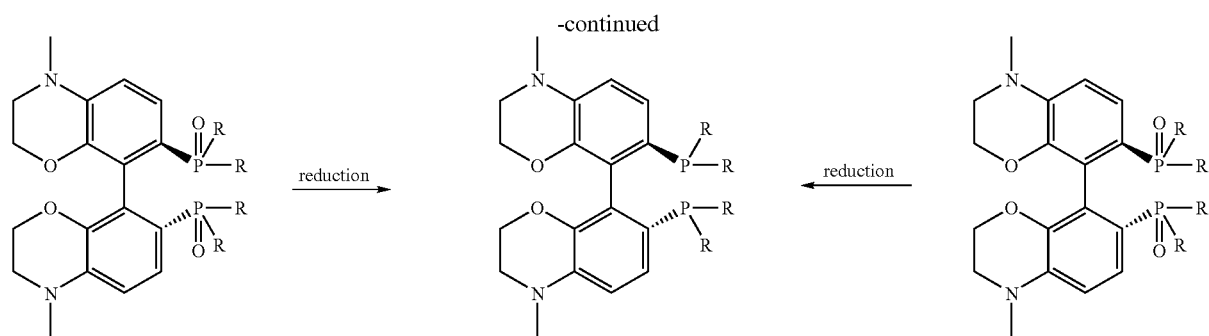
Route 2' Via Biaryl with Alternative Ring Closure and Resolution of Racemate Via Diastereomers:
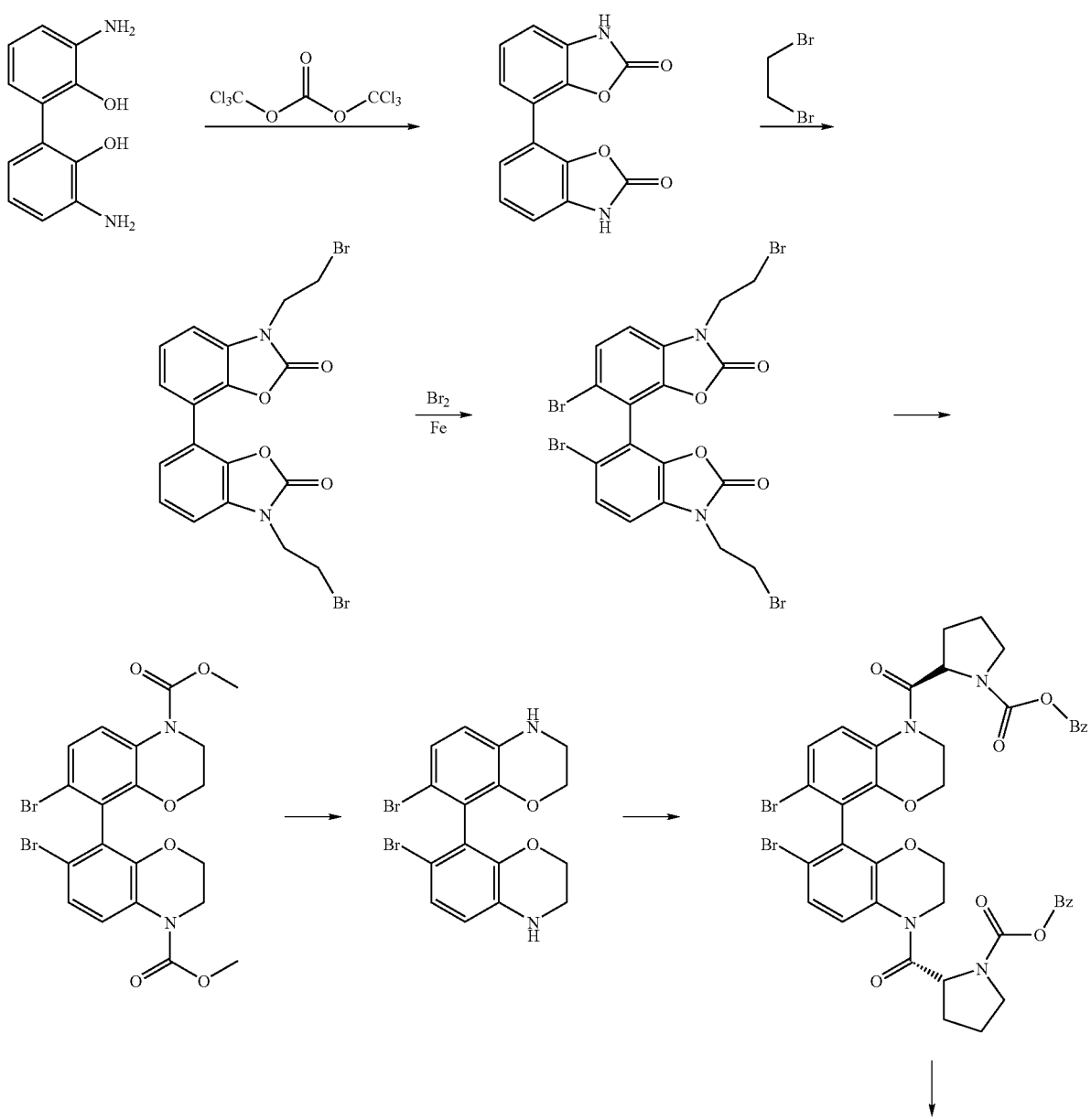

-continued
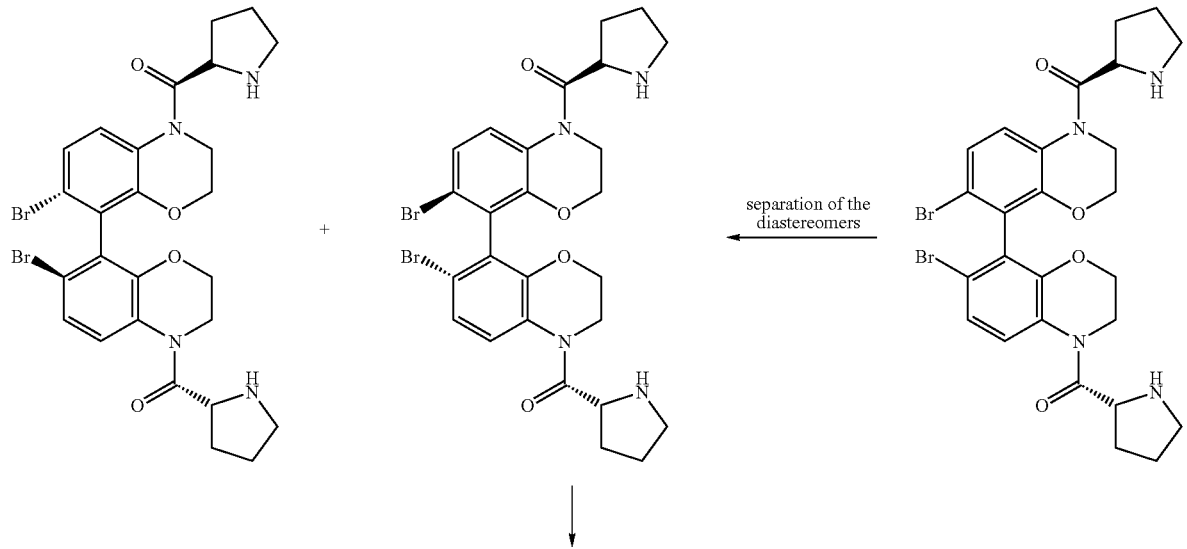
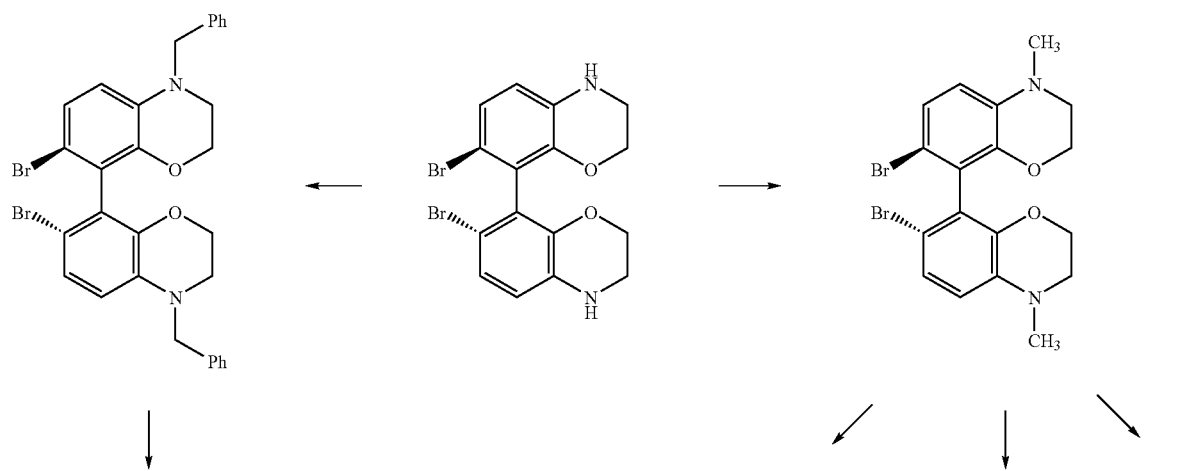
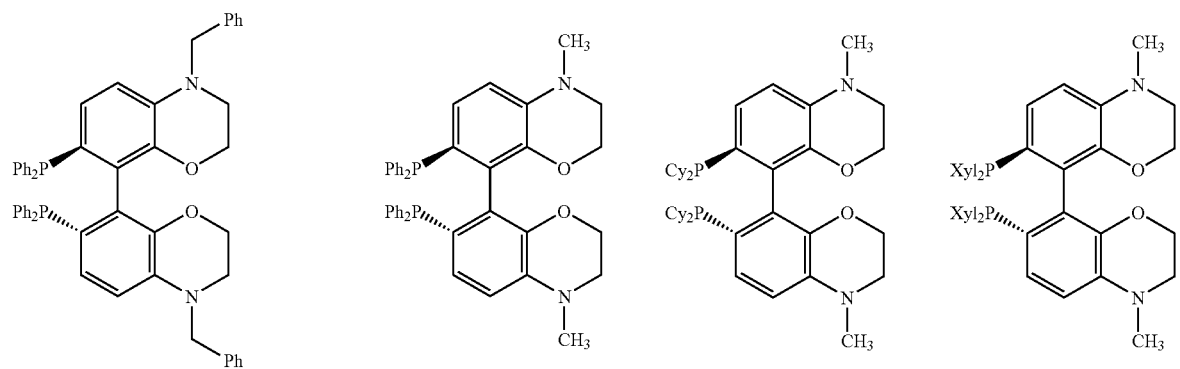

Route 3 Via Biaryl: Alternative Resolution of Racemate (for Example Chiral HPLC)
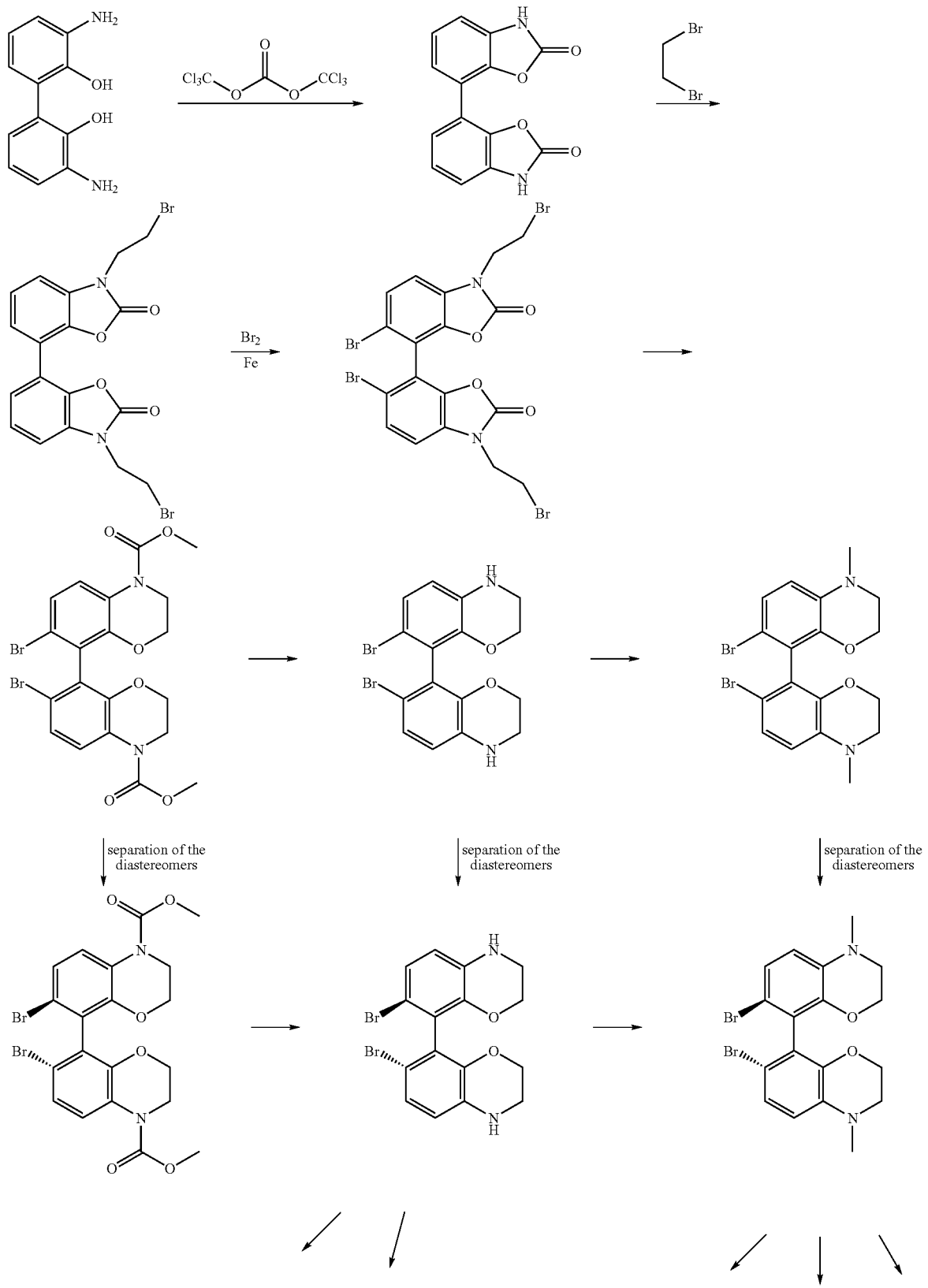

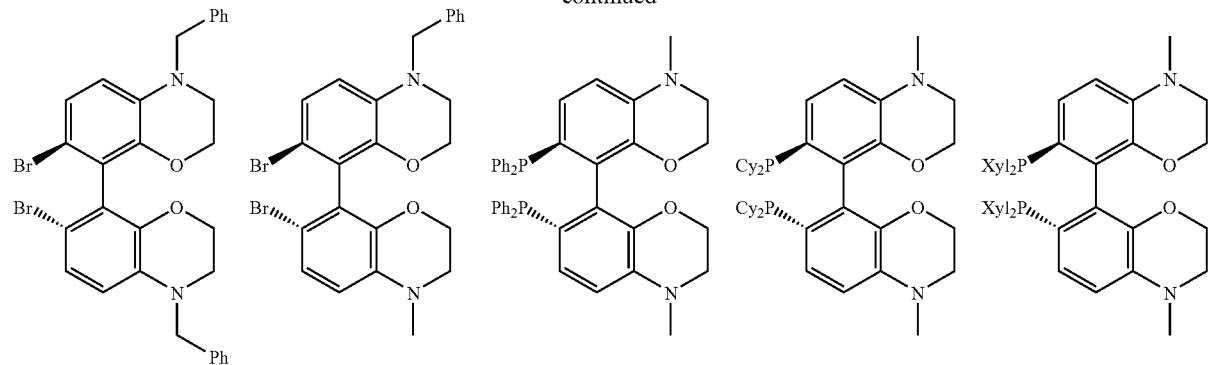
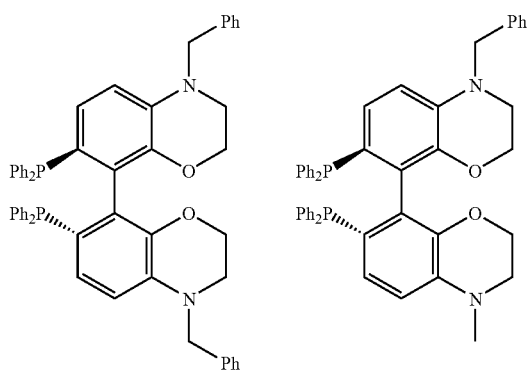
Preparation of Unsymmetrical Compounds:
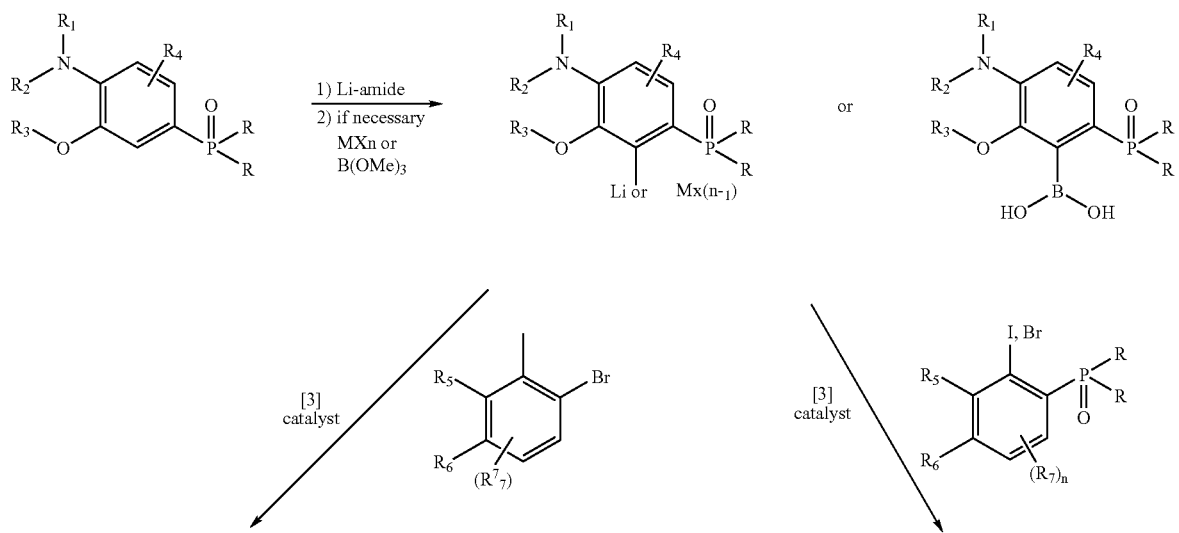

41
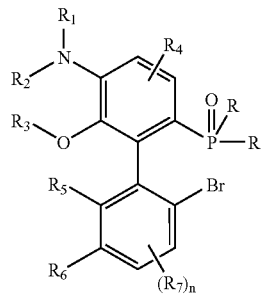
1) R—Li
2) Cl—PRR
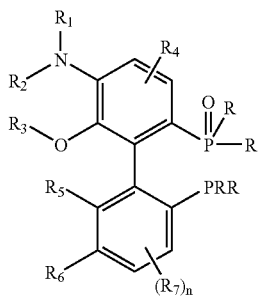
optical resolution
HPLC
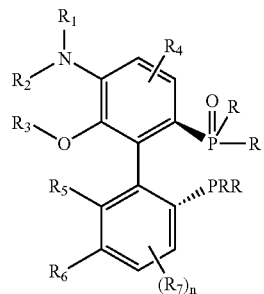
reduction
HSiCl₃/NBu₃
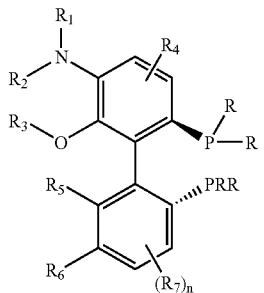
-continued
42
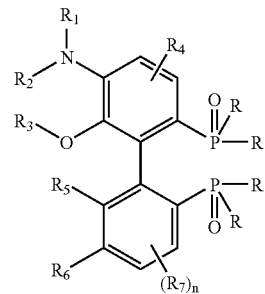
optical resolution
HPLC
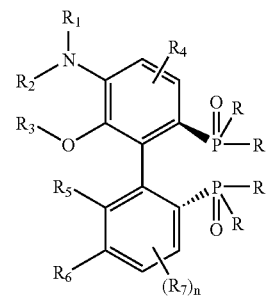
reduction
HSiCl₃/NBu₃

Unsymmetrically Substituted Compounds can Also be Obtained According to the Following Scheme:

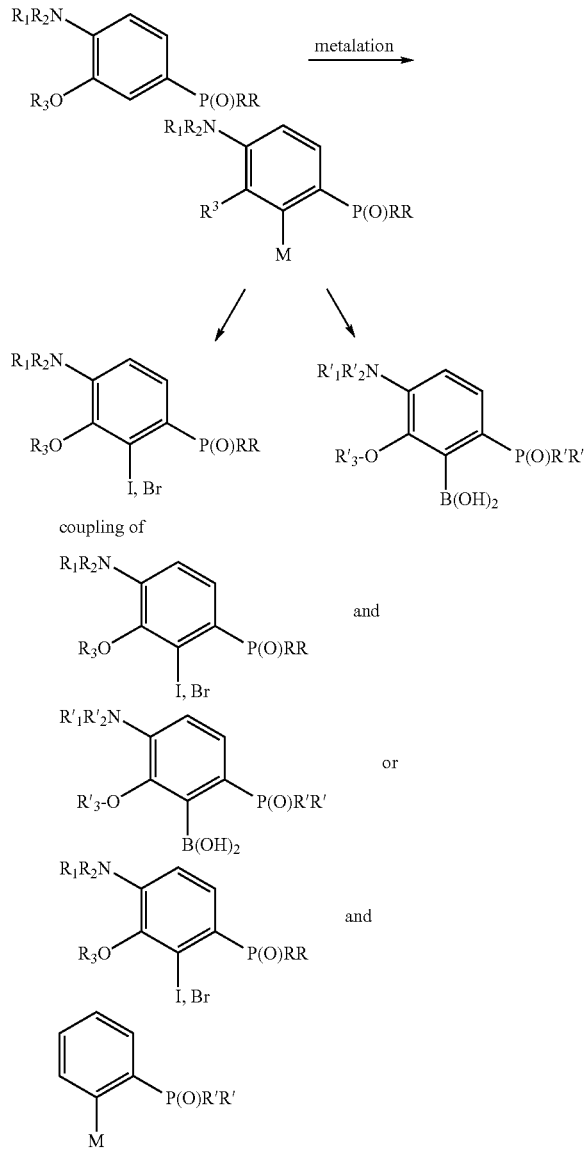

The novel compounds of the formula I are ligands for complexes of metals selected from the group of the TM8 metals, in particular from the group consisting of Ru, Rh and Ir, which are excellent catalysts or catalyst precursors for asymmetric syntheses, for example the asymmetric hydrogenation of prochiral, unsaturated, organic compounds. If prochiral unsaturated organic compounds are used, a very high excess of optical isomers can be induced in the synthesis of organic compounds and a high chemical conversion can be achieved in short reaction times.

The invention further provides complexes of metals selected from the group of the TM8 metals with compounds of the formulae I and Ia as ligands.

Possible metals are, for example, Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

The metal complexes can, depending on the oxidation number and coordination number of the metal atom, contain further ligands and/or anions. They can also be cationic metal complexes. Analogous metal complexes of this type and their preparation are widely described in the literature.

The metal complexes can, for example, correspond to the general formulae XI and XII, $$A_1MeL_n \qquad (XI),$$

$$(A_1MeL_n)^{(z+)}(E^-)_z \qquad (XII),$$

where
$A_1$ is a compound of the formula Ia or Ib,
L represents identical or different monodentate, anionic or nonionic ligands, or two L form identical or different bidentate, anionic or nonionic ligands;
n is 2, 3 or 4 when L is a monodentate ligand or n is 1 or 2 when L is a bidentate ligand;
z is 1, 2 or 3;
Me is a metal selected from the group consisting of Rh and Ir; with the metal having the oxidation state 0, 1, 2, 3 or 4;
$E^-$ is the anion of an oxo acid or complex acid; and
the anionic ligands balance the charge of the oxidation stage 1, 2, 3 or 4 of the metal.

The above-described preferences and embodiments apply to the compounds of the formula XI and XII.

Monodentate nonionic ligands can, for example, be selected from the group consisting of olefins (for example ethylene, propylene), allyls (allyl, 2-methallyl), solvating solvents (nitriles, linear or cyclic ethers, unalkylated or N-alkylated amides and lactams, amines, phosphines, alcohols, carboxylic esters, sulfonic esters), nitrogen monoxide and carbon monoxide.

Monodentate anionic ligands can, for example, be selected from the group consisting of halide (F, Cl, Br, I), pseudohalide (cyanide, cyanate, isocyanate) and anions of carboxylic acids, sulfonic acids and phosphonic acids (carbonate, formate, acetate, propionate, methylsulfonate, trifluoromethylsulfonate, phenylsulfonate, tosylate).

Bidentate nonionic ligands can, for example, be selected from the group consisting of linear or cyclic diolefins (for example hexadiene, cyclooctadiene, norbornadiene), dinitriles (malononitrile), unalkylated or N-alkylated diamides of carboxylic acids, diamines, diphosphines, diols, acetonylacetonates, dicarboxylic diesters and disulfonic diesters.

Bidentate anionic ligands can, for example, be selected from the group consisting of the anions of dicarboxylic acids, disulfonic acids and diphosphonic acids (for example of oxalic acid, malonic acid, succinic acid, maleic acid, methylenedisulfonic acid and methylenediphosphonic acid).

Preferred metal complexes also include ones in which E is —Cl$^-$, —Br$^-$, —I$^-$, ClO$_4^-$, CF$_3$SO$_3^-$, CH$_3$SO$_3^-$, HSO$_4^-$, BF$_4^-$, B(phenyl)$_4^-$, B(C$_6$F$_5$)$_4^-$, B(3,5-bistrifluoromethylphenyl)$_4^-$, PF$_6^-$, SbCl$_6^-$, AsF$_6^-$ or SbF$_6^-$.

Very particularly preferred metal complexes, which are particularly suitable for hydrogenations, correspond to the formulae XIII and XIV, $$[A_1Me_1YZ] \qquad (XIII),$$

$$[A_1Me_1Y]^+E_1^- \qquad (XIV),$$

where
$A_1$ is a compound of the formula Ia or Ib;
$Me_1$ is rhodium or iridium;
Y represents two olefins or one diene;
Z is Cl, Br or I; and
$E_1^-$ is the anion of an oxo acid or complex acid.

The above-described embodiments and preferences apply to the compounds of the formulae Ia and Ib.

Olefins as Y can be $C_2$-$C_{12}$-, preferably $C_2$-$C_6$- and particularly preferably $C_2$-$C_4$-olefins. Examples are propene, 1-butene and in particular ethylene. The diene can contain from 5 to 12, preferably from 5 to 8, carbon atoms and can be an open-chain, cyclic or polycyclic diene. The two olefin groups of the diene are preferably connected by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylene molecules or 1,5-hexadiene, 1,5-cyclooctadiene or norbornadiene.

In the formula XIII, Z is preferably Cl or Br. Examples of $E_1$ in the formula XIV are $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

Ruthenium complexes according to the invention can, for example, correspond to the formula XV,

$$[Ru_aH_bZ_c(A_1)_dL_e]_f(E^k)_g(S)_h \qquad (XV),$$

where

Z is Cl, Br or I; $A_1$ is a compound of the formula I or Ia; L represents identical or different ligands; $E^-$ is the anion of an oxo acid, mineral acid or complex acid; S is a solvent capable of coordination as ligand; and a is from 1 to 3, b is from 0 to 4, c is from 0 to 6, d is from 1 to 3, e is from 0 to 4, f is from 1 to 3, g is from 1 to 4, h is from 0 to 6 and k is from 1 to 4, with the total charge of the complex being zero.

The abovementioned preferences for Z, $A_1$, L and $E^-$ apply to the compounds of the formula XV. The ligands L can additionally be arenes or heteroarenes (for example benzene, naphthalene, methylbenzene, xylene, cumene, 1,3,5-mesitylene, pyridine, biphenyl, pyrrole, benzimidazole or cyclopentadienyl) and metal salts which act as Lewis acids (for example $ZnCl_2$, $AlCl_3$, $TiCl_4$ and $SnCl_4$). The solvent ligands can be, for example, alcohols, amines, acid amides, lactams and sulfones.

Complexes of this type are described in the references mentioned below and the references cited therein:

D. J. Ager, S. A. Laneman, Tetrahedron: Asymmetry, 8, 1997, 3327-3355;

T. Ohkuma, R. Noyori in Comprehensive Asymmetric Catalysis (E. N. Jacobsen, A. Pfaltz, H. Yamamoto, Eds.), Springer, Berlin, 1999,199-246;

J. M. Brown in Comprehensive Asymmetric Catalysis (E. N. Jacobsen, A. Pfaltz, H. Yamamoto, Eds.), Springer, Berlin, 1999, 122-182;

T. Ohkuma, M. Kitamura, R. Noyori in Catalytic Asymmetric Synthesis, $2^{nd}$ Edition (I. Ojima, Ed.), Wiley-VCH New York, 2000, 1-110;

N. Zanetti, et al. Organometallics 15, 1996, 860.

More specific ruthenium complexes having corresponding formulae but different diphosphine ligands are described in the following references:

$[Ru_aH_bCl_c(A_1)_d arene_e](amine)_h$: EP-A1-0 269 395 and EP-A1-0174 057;

$[Ru_a(A_1)]E^-$, more specifically $[Ru(A_1)]E^-$ and $[RuH((A_1))]E^-$: EP-A1-0 256 634;

$[Ru(A_1)(carboxylate)_1]$: US-A-4 739 084 and AP-A1-0 245 959;

$[Ru(A_1)_2(Lewis\ acid)](NC_2H_5)_3$, $[Ru(A_1)_2(Lewis\ acid)](acetate)$: EP-A1-0 307 168;

$[RuZ(arene)(A_1)]halide$, $[Ru(Z)(arene)(A_1)]E^-$: EP-A1-0 366 390;

$[RuZ_2(A_1)(chiral\ amine)]$: H. Doucet et al., Angew. Chem. Int. Ed. 37, 1998, 1703; T. Ohkuma, et al., J. Am. Chem. Soc., 120, 1998 13529; T. Ohkuma, et al., J. Am. Chem. Soc., 122, 2000, 6510.

$[RuZ_2(A_1)(pyridine)_2]$: O. M. Akotsi et al., Chirality, 12 (2000) 514.

Some specific and preferred ruthenium complexes are: [Ru(acetate)$_2$(A$_1$)], [Ru(OOCCF$_3$)$_2$(A$_1$)], [RuCl$_2$(A$_1$)], [RuBr$_2$(A$_1$)], [RuI$_2$(A$_1$)], [Ru$_2$Cl$_4$(A$_1$)$_2$](Nethyl$_3$), [Ru$_2$Cl$_4$(A$_1$)$_2$]-(Nethyl$_3$)(xylene), [RuCl(benzene)(A$_1$)]Cl, [RuBr(benzene)(A$_1$)]Br, [RuI(benzene)(A$_1$)]I, [RuCl(p-cumene)(A$_1$)]Cl, [RuBr(p-cumene)(A$_1$)]Br, [RuI(p-cumene)(A$_1$)]I, [Ru(2-methallyl)$_2$(A$_1$)], [RuCl$_2$(phenylCN)$_2$(A$_1$)], [Ru(A$_1$)(AcO)$_2$(ethanol)$_1$], [(Cp)Ru(A$_1$)]Cl, [(Cp)Ru(A$_1$)]PF$_6$, [RuCl(Pphenyl$_3$)(A$_1$)]$_2$(η-Cl)$_2$, [RuCl$_2$(A$_1$)(dpen)] and [RuCl$_2$(A$_1$)(daipen)]. Cp is cyclopentadienyl. dpen and daipen are chiral ethylenediamines, for example 1,2-diphenylethylene-1,2-diamine or 1,1-di(p-methoxyphenyl)2-isopropylethylene-1,2-diamine.

The metal complexes of the invention are prepared by methods known from the literature (cf. U.S. Pat. No. 5,371,256, U.S. Pat. No. 5,446,844, U.S. Pat. No. 5,583,241, and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts, or catalyst precursors which can be activated under the reaction conditions, which can be used for asymmetric addition reactions onto prochiral, unsaturated, organic compounds.

The metal complexes can, for example, be used for the asymmetric hydrogenation (addition of hydrogen) of prochiral compounds having carbon-carbon or carbon-heteroatom double bonds. Such hydrogenations using soluble homogeneous metal complexes are described, for example, in Pure and Appl. Chem., Vol. 68, No.1, pp. 131-138 (1996). Preferred unsaturated compounds to be hydrogenated contain the groups C=C, C=N and/or C=O. According to the invention, metal complexes of ruthenium, rhodium and iridium are preferably used for the hydrogenation.

The metal complexes of the invention can also be used as catalysts for the asymmetric hydroboration (addition of boron hydrides) of prochiral organic compounds having carbon-carbon double bonds. Such hydroborations are described, for example, by Tamio Hayashi in E. Jacobsen, A. Pfaltz, H. Yamamoto (Eds.), Comprehensive Asymmetric Catalysis I to III, Springer Verlag, Berlin, 1999, pages 351 to 364. Suitable boron hydrides are, for example, catecholboranes. The chiral boron compounds can be used in syntheses and/or be converted in a manner known per se into other chiral organic compounds which are valuable buiding blocks for the preparation of chiral intermediates or active substances. An example of such a reaction is the preparation of 3-hydroxytetrahydrofuran (as described in DE 19,807,330).

The metal complexes of the invention can also be used as catalysts for the asymmetric hydrosilylation (addition of silanes) of prochiral organic compounds having carbon-carbon or carbon-heteroatom double bonds. Such hydrosilylations are described, for example, by G. Pioda and A. Togni in Tetrahedron: Asymmetry, 1998, 9, 3093 or by S. Uemura, et al. in Chem. Commun. 1996, 847. Suitable silanes are, for example, trichlorosilane or diphenylsilane. The hydrosilylation of, for example, C=O— and C=N— groups is preferably carried out using metal complexes of rhodium and iridium. The hydrosilylation of, for example, C=C groups is preferably carried out using metal complexes of palladium. The chiral silyl compounds can be used in syntheses and/or be converted in a manner known per se into other chiral organic compounds which are valuable building blocks for the preparation of chiral intermediates or active substances. Examples of such reactions are hydrolyses to form alcohols.

The metal complexes of the invention can also be used as catalysts for asymmetric allylic substitution reactions (addition of carbon nucleophiles onto allyl compounds. Such allylations are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884. Suitable precursors for allyl compounds are, for example, 1,3-diphenyl-3-acetoxy-1-propene or 3-acetoxy-1-cyclohexene. Metal complexes of palladium are preferably used for this reaction. The chiral allyl compounds can be used in syntheses for preparing chiral intermediates or active substances.

The metal complexes of the invention can also be used as catalysts for the asymmetric amination (addition of amines onto allyl compounds) or etherification (addition of alcohols or phenols onto allyl compounds). Such aminations and etherifications are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884. Suitable amines include ammonia and primary and secondary amines. Suitable alcohols are phenols and aliphatic alcohols. Metal complexes of palladium are preferably used for the amination or etherification of the allyl compounds. The chiral amines and ethers can be used in syntheses for preparing chiral intermediates or active substances.

The metal complexes of the invention can also be used as catalysts for asymmetric isomerization, cf. M. Beller et al. in Transition Metals for Organic Synthesis, Volume 1, Wiley-VCH, Weinheim 1998, pages 147-156.

The invention further provides for the use of the metal complexes of the invention as homogeneous catalysts for preparing chiral organic compounds by asymmetric addition of hydrogen, boron hydrides or silanes onto a carbon-carbon or carbon-heteroatom multiple bond in prochiral organic compounds, or the asymmetric addition of carbon nucleophiles or amines onto allyl compounds.

A further aspect of the invention is a process for preparing chiral organic compounds by assymetric addition of hydrogen, boron hydrides or silanes onto a carbon-carbon or carbon-heteroatom multiple bond in prochiral organic compounds, or the asymmetric addition of carbon nucleophiles, alcohols or amines onto allyl compounds in the presence of a catalyst, which is characterized in that the addition reaction is carried out in the presence of catalytic amounts of at least one metal complex according to the invention.

Preferred prochiral, unsaturated compounds to be hydrogenated can contain one or more, identical or different C=C, C=N and/or C=O groups in open-chain or cyclic organic compounds, with the C=C, C=N and/or C=O groups being able to be part of a ring system or being exocyclic groups. The prochiral unsaturated compounds can be alkenes, cycloalkenes, heteroalkenes and also open-chain or cyclic ketones, ketimines and kethydrazones. They can, for example, correspond to the formula XVI, $$R_{15}R_{16}C=D \qquad (XVI),$$

where $R_{15}$ and $R_{16}$ are selected so that the compound is prochiral and are each, independently of one another, an open-chain or cyclic hydrocarbon radical or heterohydrocarbon radical containing heteroatoms selected from the group consisting of O, S and N and each have from 1 to 30, preferably from 1 to 20, carbon atoms;

D is O or a radical of the formula $CR_{17}R_{18}$ or $NR_{19}$;

$R_{17}$ and $R_{18}$ are each, independently of one another, defined as for $R_{15}$ and $R_{16}$, $R_{19}$ is hydrogen, $C_1$-$C_{12}$-alkyl, $C_1$-$C_{12}$-alkoxy, $C_3$-$C_{12}$-cycloalkyl, $C_3$-$C_{12}$-cycloalkyl-$C_1$-$C_6$-alkyl, $C_3$-$C_{11}$-heterocycloalkyl, $C_3$-$C_{11}$-heterocycloalkyl-$C_1$-$C_6$-alkyl, $C_6$-$C_{14}$-aryl, $C_5$-$C_{13}$-heteroaryl, $C_7$-$C_{16}$-aralkyl or $C_6$-$C_{14}$-heteroaralkyl, $R_{15}$ and $R_{16}$ together with the carbon atom to which they are bound form a hydrocarbon ring or heterohydrocarbon ring having from 3 to 12 ring atoms;

$R_{15}$ and $R_{17}$ together with the C=C group to which they are bound form a hydrocarbon ring or heterohydrocarbon ring having from 3 to 12 ring atoms;

$R_{15}$ and $R_{19}$ together with the C=N group to which they are bound form a hydrocarbon ring or heterohydrocarbon ring having from 3 to 12 ring atoms;

the heteroatoms in the heterocyclic rings are selected from the group consisting of O, S and N;

and $R_{15}$, $R_{16}$, $R_{17}$, $R_{18}$ and $R_{19}$ are unsubstituted or substituted by $C_1$-$C_6$-alkyl, $C_1$-$C_6$-alkoxy, cyclohexyl, $C_6$-$C_{10}$-aryl, $C_7$-$C_{12}$-aralkyl, $C_1$-$C_4$-alkyl-$C_6$-$C_{10}$-aryl, $C_1$-$C_4$-alkoxy-$C_6$-$C_{10}$-aryl, $C_1$-$C_4$-alkyl-$C_7$-$C_{12}$-aralkyl, $C_1$-$C_4$-alkoxy-$C_7$-$C_{12}$-aralkyl, —OH, =O, —$NR_{21}R_{122}$, —CO—$OR_{20}$ or —CO—$NR_{21}R_{22}$, where $R_{20}$ is H, an alkali metal, $C_1$-$C_6$-alkyl, cyclohexyl, phenyl or benzyl and $R_{21}$ and $R_{22}$ are each, independently of one another, hydrogen, $C_1$-$C_6$-alkyl, cyclohexyl, phenyl or benzyl, or $R_{21}$ and $R_{22}$ together are tetramethylene, pentamethylene or 3-oxapentylene.

Examples and preferences for substituents have been mentioned above.

$R_{15}$ and $R_{16}$ can be, for example, $C_1$-$C_{20}$-alkyl and preferably $C_1$-$C_{12}$-alkyl, $C_1$-$C_{20}$-heteroalkyl and preferably $C_1$-$C_{12}$-heteroalkyl containing heteroatoms selected from the group consisting of O, S and N, $C_3$-$C_{12}$-cycloalkyl and preferably $C_4$-$C_8$-cycloalkyl, C-bonded $C_3$-$C_{11}$-heterocycloalkyl and preferably $C_4$-$C_8$-heterocycloalkyl containing heteroatoms selected from the group consisting of O, S and N, $C_3$-$C_{12}$-cycloalkyl-$C_1$-$C_6$-alkyl and preferably $C_4$-$C_8$-cycloalkyl-$C_1$-$C_6$-alkyl, $C_3$-$C_{11}$-heterocycloalkyl-$C_1$-$C_6$-alkyl and preferably $C_4$-$C_8$-heterocycloalkyl-$C_1$-$C_6$-alkyl containing heteroatoms selected from the group consisting of O, S and N, $C_6$-$C_{14}$-aryl and preferably $C_6$-$C_{10}$-Aryl, $C_5$-$C_{13}$-heteroaryl and preferably $C_5$-$C_9$-heteroaryl containing heteroatoms selected from the group consisting of O, S and N. $C_7$-$C_{15}$-aralkyl and preferably $C_7$-$C_{11}$-aralkyl, $C_6$-$C_{12}$-heteroaralkyl and preferably $C_6$-$C_{10}$-heteroaralkyl containing heteroatoms selected from the group consisting of O, S and N.

If $R_{15}$ and $R_{16}$, $R_{15}$ and $R_{17}$, or $R_{15}$ and $R_{19}$ together with the group to which they are bound form a hydrocarbon ring or heterohydrocarbon ring, the ring preferably contains from 4 to 8 ring atoms. The heterohydrocarbon ring can contain, for example, from 1 to 3, preferably one or two, heteroatoms.

$R_{19}$ is preferably hydrogen, $C_1$-$C_6$-alkyl, $C_1$-$C_6$-alkoxy, $C_4$-$C_8$-cycloalkyl, $C_4$-$C_8$-cycloalkyl-$C_1$-$C_4$-alkyl, $C_4$-$C_{10}$-heterocycloalkyl, $C_4$-$C_{10}$-heterocycloalkyl-$C_1$-$C_4$-alkyl, $C_6$-$C_{10}$-aryl, $C_5$-$C_9$-heteroaryl, $C_7$-$C_{12}$-aralkyl and $C_5$-$C_{13}$-heteroaralkyl.

Some examples of unsaturated organic compounds are acetophenone, 4-methoxy-acetophenone, 4-trifluoromethylacetophenone, 4-nitroacetophenone, 2-chloroacetophenone, corresponding unsubstituted or N-substituted acetophenone benzylimines, unsubstituted or substituted benzocyclohexanone or benzocyclopentanone and corresponding imines, imines from the group consisting of unsubstituted or substituted tetrahydroquinoline, tetrahydropyridine and dihydropyrrole, and unsaturated carboxylic acids, carboxylic esters, carboxamides and carboxylic acid salts, for example α- and, if appropriate, β-substituted acrylic acids or crotonic acids. Preferred carboxylic acids are carboxylic acids of the formula

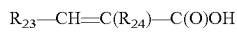

$R_{23}$—CH=C($R_{24}$)—C(O)OH and also their salts, esters and amides, where $R_{23}$ is $C_1$-$C_6$-alkyl, unsubstituted $C_3$-$C_8$-cycloalkyl or $C_3$-$C_8$-cycloalkyl substituted by from 1 to 4 $C_1$-$C_6$-alkyl, $C_1$-$C_6$-alkoxy or $C_1$-$C_6$-alkoxy-$C_1$-$C_4$-alkoxy groups or unsubstituted $C_6$-$C_{10}$-aryl or $C_6$-$C_{10}$-aryl substituted by from 1 to 4 $C_1$-$C_6$-alkyl, $C_1$-$C_6$-alkoxy or $C_1$-$C_6$-alkoxy-$C_1$-$C_4$-alkoxy groups, preferably phenyl, and $R_{24}$ is linear or branched $C_1$-$C_6$-alkyl (for example isopropyl), unsubstituted cyclopentyl, cyclohexyl or phenyl or cyclopentyl, cyclohexyl or phenyl substituted as defined above or protected amino (for example acetylamino).

Further suitable substrates for the hydrogenation are, for example, prochiral allyl alcohols and β-enamides. Particularly suitable substrates for the hydrogenation using ruthenium complexes are, for example prochiral α- and β-ketocarboxylic acid salts, esters and amides, 1,3-diketones and prochiral ketones, α- and β-alkoxyketones and α- and β-hydroxyketones, α- and β-haloketones and α- and β-aminoketones.

The process of the invention can be carried out at low or elevated temperatures, for example temperatures of from −20 to 150° C., preferably from −10 to 100° C., and particularly preferably from 10 to 80° C. The optical yields are generally better at relatively low temperature than at higher temperatures.

The process of the invention can be carried out at atmospheric pressure or under superatmospheric pressure. The pressure can be, for example, from $10^5$ to $2\times10^7$ Pa (pascal). Hydrogenations are preferably carried out at superatmospheric pressure.

Catalysts are preferably used in amounts of from 0.00001 to 10 mol %, particularly preferably from 0.0001 to 10 mol %, and very particularly preferably from 0.001 to 5 mol %, based on the compound to be hydrogenated.

The preparation of the catalysts and also the hydrogenations and addition reactions can be carried out without solvent or in the presence of an inert solvent, with it being possible to use one solvent or mixtures of solvents. Suitable solvents have been mentioned above.

The reactions can be carried out in the presence of cocatalysts, for example quaternary ammonium halides (tetrabutylammonium iodide) and/or in the presence of protic acids, for example mineral acids (cf. for example, U.S. Pat. No. 5,371, 256, U.S. Pat. No. 5,446,844 and U.S. Pat. No. 5,583,241 and EP-A-0 691 949). The cocatalysts are particularly useful for hydrogenations.

The metal complexes used as catalysts can be added as separately prepared isolated compounds or can be formed in situ prior to the reaction and then be mixed with the substrate to be hydrogenated. It can be advantageous to add additional ligands in the reaction using isolated metal complexes or to use an excess of ligands in the in-situ preparation. The excess can be, for example, from 1 to 10 mol, preferably from 1 to 5 mol, based on the metal compound used for the preparation. In the case of the in situ preparation of the catalysts, it is also possible to use salts of the diphosphine ligands, for example halides or tetrafluoroborates.

The process of the invention is generally carried out by firstly placing the catalyst in a reaction vessel and then adding the substrate, if desired reaction auxiliaries and the compound to be added on, and then starting the reaction. Gaseous compounds to be added on, for example hydrogen or ammonia, are preferably injected under pressure. The process can be carried out continuously or batchwise in various types of reactor.

The chiral organic compounds which can be prepared according to the invention are active substances or intermediates for the preparation of such substances, in particular in the field of preparation of pharmaceuticals and agrochemicals. Thus, for example, o,o-dialkylaryl-ketamine derivatives, in particular those bearing alkyl and/or alkoxyalkyl groups, act as fungicides, in particular as herbicides. The derivatives can be amine salts, acid amides, e.g. of chloroacetic acid, tertiary amines and ammonium salts (cf., for example, EP-A-0 077 755 and EP-A-0 115 470).

The following examples illustrate the invention.

A) Preparation of Intermediates

EXAMPLE A1

Preparation of Compounds of the Formula

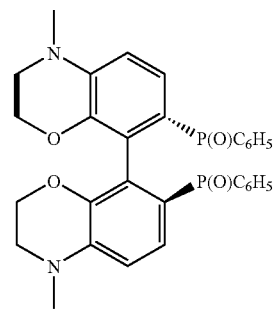

a) Preparation of
2,2'-dihydroxy-3,3'-diaminobiphenyl (2)

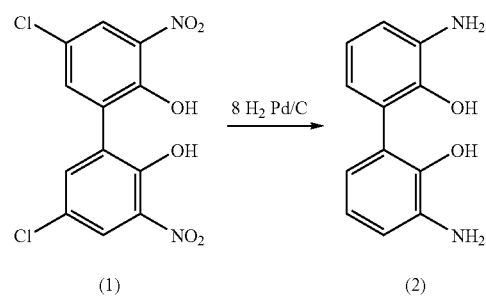

10 g of niclofolan (1) are dissolved in 100 ml of tetrahydrofuran (THF) and 17.6 g of triethylamine. After addition of 4 g of palladium on carbon 5% and a further 4 g after 40 hours, hydrogenation is carried out to saturation over a total period of about 88 hours. The solution is filtered through Hyflo and is immediately processed further without evaporation. Assumed yield of (2): 100%. $R_f$ 0.11 ($CH_2Cl_2$/methanol/$NH_4OH$ 25% (60:10:1))

$^1$H-NMR (300 MHz, (CD$_3$)$_2$SO): 6.68 (2H, m), 6.48 (4H, m).

b) Preparation of Compound (3)

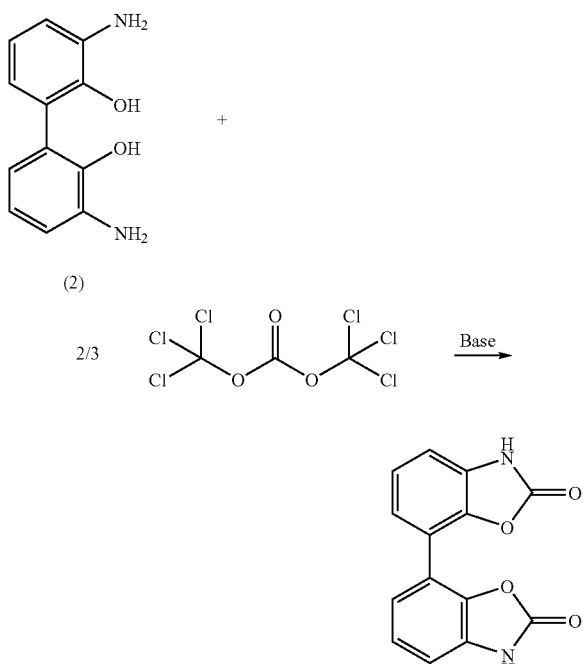

The filtered solution from the hydrogenation comprising (2), which already contains sufficient triethylamine, is cooled in ice and a solution of 5.67 g of triphosgene in 10 ml of THF is quickly added dropwise. The mixture is firstly stirred at 0° C. for 30 minutes and subsequently at room temperature (RT) for 1 hour. The product is precipitated by means of water, acidified with 4N HCl and then filtered off. The dried crystals are digested with methanol and filtered off with suction. This gives 4.9 g of brown crystals of the compound (3) (64% of theory), melting point: >270° C.; R$_f$ 0.45 (CH$_2$Cl$_2$/MeOH/ NH$_4$OH 25% (60:10:1)). $^1$H-NMR (300 MHz, (CD$_3$)$_2$SO): 11.85 (2H, s), 7.35 (2H, d), 7.29 (2 H, t), 7.15 (2 H, d).

c) Preparation of Compound (4)

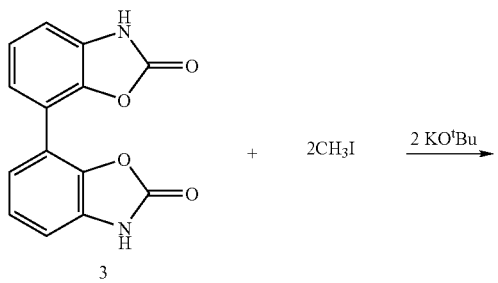

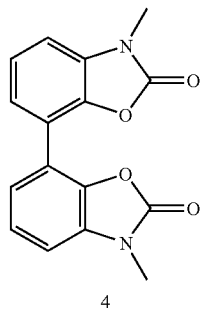

35 g of the carbamate (3) are dissolved in 700 ml of dimethylformamide (DMF) and 32.2 g of potassium tert-butoxide are added a little at a time at 15-20° C. (ice bath). After stirring for one hour at RT, 17.9 ml of methyl iodide are added at 8° C. This results in the temperature rising to 12° C. The mixture is stirred at RT for 2 days and another 0.1 equivalent of base and 0.1 equivalent of methyl iodide are then added. After stirring at RT for 1 hour and then briefly heating to 50° C., the suspension is evaporated. The residue is stirred with about 500 ml of water and filtered off with suction. This gives 37.07 g of the compound (4) in the form of a fine brown powder. (96%, of theory).

Melting point >270° C.; R$_f$ 0.60 (toluene/ethyl acetate/ CH$_2$Cl$_2$/formic acid (24:40:40:4)).

$^1$H-NMR (300 MHz, (CDCl$_3$): 7.59 (2H, d), 7.40 (2H, t) 7.0 (2H, d), 3.45 (6H, s).

d) Preparation of Compound (5)

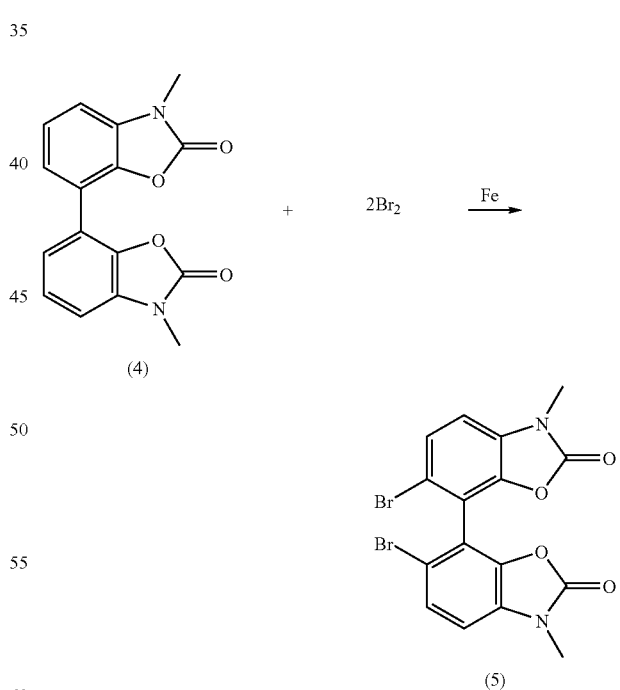

37 g of the methylated carbamate (4) are dissolved in 260 ml of nitrobenzene at 200° C. After addition of 250 mg of iron powder, 14 ml of bromine are dissolved in a little nitrobenzene, added dropwise at 150-180° C. over a period of 25 minutes and the mixture is stirred at 160° C.-100° C. for 2 hours. A further 5 ml of bromine are then added and the mixture is stirred at 80° C. for another 1 hour. After cooling to RT, which results in the product beginning to precipitate, the crude product is isolated virtually quantitatively by addition of 300 ml of petroleum ether and 300 ml of diethyl ether and subsequent filtration. The crude product is briefly heated with 150 ml of acetonitrile and then filtered off with suction at RT. Drying in a high vacuum/80° C. gives 37.1 g (65% of theory) of the isomerically pure product (5) as brown fine crystals.

Melting point >270° C.; $R_f$ 0.65 (toluene/ethyl acetate/ $CH_2Cl_2$/formic acid (24:40:40:4)).

$^1$H-NMR (300 MHz, (CDCl$_3$): 7.56 (2H, d), 6.95 (2H, d), 3.43 (6H, s).

e) Preparation of Compound (7)

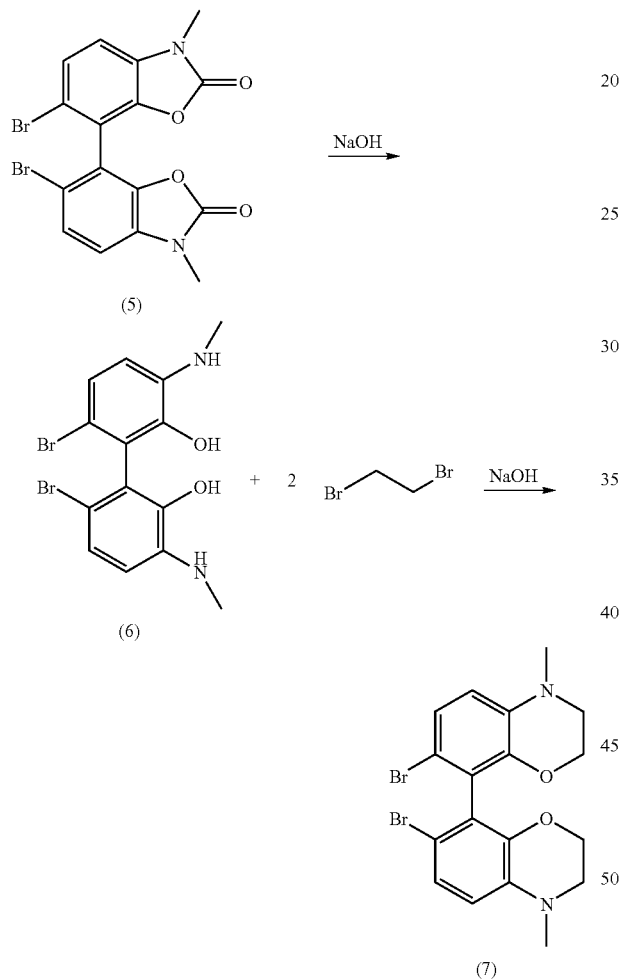

38 g of the dibromocarbamate (5) are dissolved together with 400 mg of 2,6-di-t-butyl4-methylphenol (BHT): in 590 ml of dimethyl sulfoxide (DMSO) at 95° C. and the mixture is stirred at this temperature together with 200 ml of 2N aqueous sodium hydroxide solution under argon/with exclusion of light for 15-30 minutes (HPLC monitoring). The aminophenol intermediate (6) obtained in this way is immediately processed further firstly cooled and at an internal temperature of 7° C. admixed with 144 ml of dibromoethane. After 10 minutes, the ice bath is removed and the mixture is stirred at RT for another 21 hours. It is then allowed to react at 95° C. for 2 hours. The reaction mixture is diluted with water and then extracted twice with $CH_2Cl_2$ and washed twice with water. The organic phase is dried over MgSO$_4$ and evaporated to dryness. 56 g of crude product are separated on 500 g of silica gel (40-63 μm) using $CH_2Cl_2$/petroleum ether (4:1). The substance is then taken up on 60 g of silica gel ($CH_2Cl_2$). The combined pure fractions (22.5 g) are digested with cold methanol, filtered off with suction and dried at 50° C. in a high vacuum for 3 days. This gives 20.9 g of pure, white crystals of the compound (7) (55% of theory).

Melting point 211-213° C.; $R_f$ 0.39 [$CH_2Cl_2$/petroleum ether (30-50 4:1)]. $^1$H-NMR (300 MHz, (CDCl$_3$): 7.12 (2H, d), 6.58 (2H, d), 4.23 (4H, t), 3.38-3.28 (4H, m). 2.95 (6H, m).

f) Preparation of Compound (8)

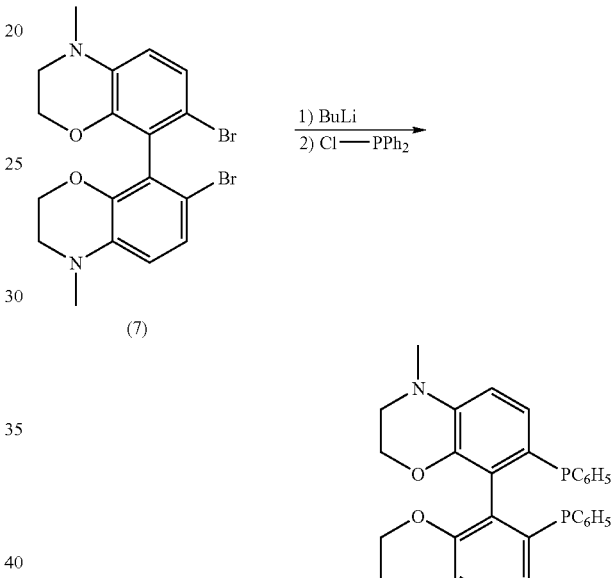

10 ml n-butylLi (1.6 molar solution in hexane) are slowly added dropwise to a mixture of 3 g of the dibromo compound (7) and 1.8 ml of tetramethylethylenediamine (TMEDA) in 50 ml of toluene at 0-5° C. while stirring. The mixture is stirred at this temperature for 30 minutes. The mixture is subsequently cooled to −60° C. and 4.2 ml of chlorodiphenylphosphine are added dropwise over a period of 10 minutes while stirring. After stirring at −60° C. for 30 minutes, the reaction mixture is slowly allowed to warm to room temperature in the cooling bath while stirring. The resulting suspension is admixed with methylene chloride and filtered. The solution is extracted with a saturated aqueous NaHCO$_3$ solution and methylene chloride, the organic phase is dried over sodium sulfate and the solvent is removed on a rotary evaporator. Ethyl acetate is added while stirring until the product precipitates. This is filtered off, washed with methanol/ethyl acetate (5:1) and dried in a high vacuum. The product (8) is obtained as a white powder.

$^1$H-NMR (300 MHz, CDCl$_3$): 7.28-6.95 (20H, m); 6.55 (4H, m$_c$); 3.73-3.64 (2H, $^2$J=10.5, m); 3.50 (2H, ddd, $^3$J=7.5, 3.5); 3.16 (2H, ddd, $^2J$=10.5, $^3J$=7.5, 3.5); 2.81-2.78 (2H, m); 2.78 (6H, s). $^{31}$P-NMR (121.5 MHz, CDCl$_3$): −14.9 g) Preparation of Compounds of the Formula (9), Ph is phenyl

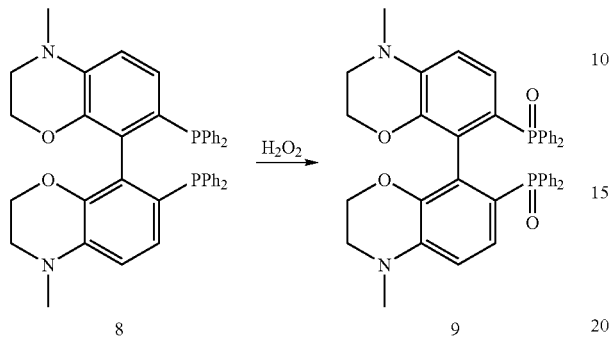

0.6 ml of hydrogen peroxide (30% in water) is slowly added dropwise to a mixture of 1.8 g of the diphosphine (8) in 25 ml of THF at 0-5° C. The reaction is exothermic. After the addition, the reaction mixture is stirred at 0-5° C. for another 10 minutes, and is then allowed to warm slowly to room temperature. After the solvent has been evaporated on a rotary evaporator, the product (9) is obtained as a light-colored solid foam.

$^1$H-NMR (300 MHz, CDCl$_3$): 7.65-7.55 (4H, m); 7.45-7.21 (12H, m); 7.21-7.09 (4H, m): 6.55 (2H, d$_p$d, $^3J$=15.0, 7.5); 6.35 (2H, d$_p$d, $^3J$=7.5, $^4J$=3.5); 3.60 (2H, ddd, $^2J$=11.3, $^3J$=3.5); 3.41 (2H, ddd, $^2J$=11.25, $^3J$=7.5, 3.5); 3.13 (2H, ddd, $^2J$=11.3, $^3J$=11.3, $^3J$=3.5) 2.85 (2H, ddd, $^2J$=11.3, $^3J$=3.5); 2.77 (6H, s). $^{31}$P-NMR (121.5 MHz, CDCl$_3$): +30.93.

h) Separation of the Enantiomers of the Compounds (9)

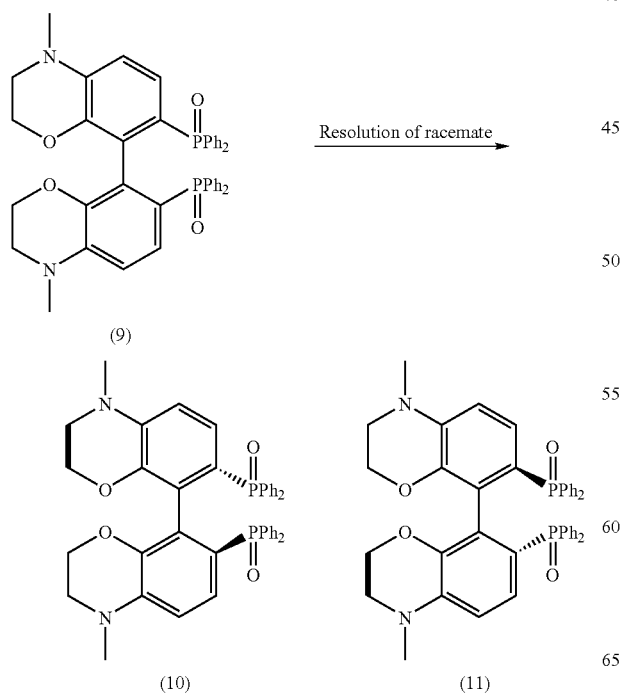

The resolution of the racemate is carried out by preparative column chromatography (HPLC); column: Chiracell OD 250×50 mm, particle size=10 mm. Hexane/isopropanol (55: 45) is used as eluent. EXAMPLE A2

Preparation of

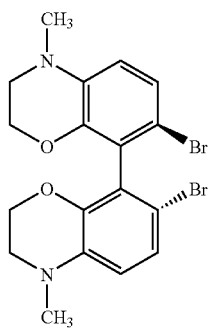
(12)

a) Preparation of

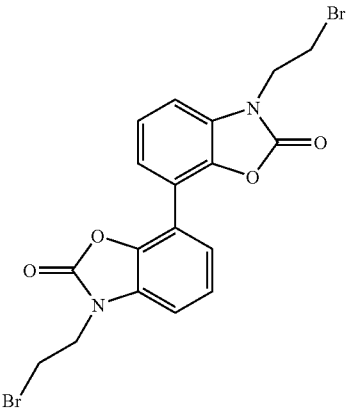
(13)

A solution of 20 g of compound 3 in 150 ml of DMF is stirred with 22.6 g of potassium carbonate for 15 minutes. 64 ml of dibromoethane are then added and the reaction mixture is stirred for 3 days. The reaction mixture is evaporated and the residue is digested with water, dried and purified by being digested again with acetonitrile. This gives 13 as a violet-brown fine powder.

$^1$H NMR (CDCl$_3$): 7.60 (dd, 2H), 7.32 (t, 2H), 7.10 (dd, 2H), 4.30 (t, 4H), 3.71(t, 4H).

b) Preparation of

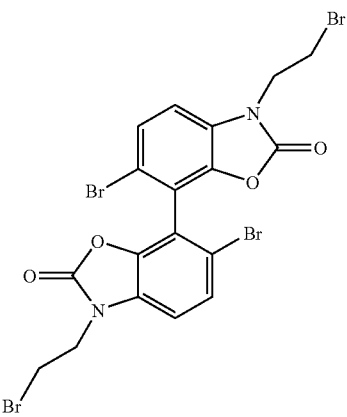
(14)

9.9 g of 13 are suspended in 90 ml of dichloromethane and admixed with 115 mg of iron powder and 2.6 ml of bromine. After stirring for 3 days, another 0.5 ml of bromine is added and the reaction mixture is stirred for a further 5 days and then worked up. The liquid phase is poured off from the tar-like residue and washed with water and NaHSO$_3$ solution. It is then extracted once with dichloromethane. The organic phase is stirred with activated carbon and silica gel, filtered and evaporated to dryness on a rotary evaporator. Digestion in ethyl acetate gives 14 as light-pink crystals.

$^1$H NMR (CDCl$_3$): 7.57 (d, 2H), 7.13 (d, 2H), 4.26 (dt, 4H), 3.70 (t, 4H).

c) Preparation of

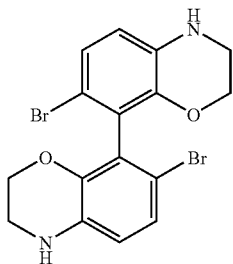

(15)

846 ml of aqueous sodium hydroxide solution (25%) are added to a suspension of 513 g of 14 and 1 g of 2,6-di-tert-butyl-4-methylphenol (BHT) in 3 l of methanol and 3 l of THF over a period of 10 minutes. This results in the temperature rising to 45° C., and the mixture is heated further to reflux and stirred at this temperature for 5 hours. The reaction mixture is partly evaporated on a rotary evaporator, admixed with 1.7 l of water, filtered with suction and the solid is washed with water and a little methanol. This gives 15 as a brown powder.

$^1$H NMR (DMSO-d6): 6.91 (d, 2H), 6.50 (d, 2H), 5.92 (s, 2H), 4.00 (m, 4H), 3.25 (q, 4H).

d) Preparation of

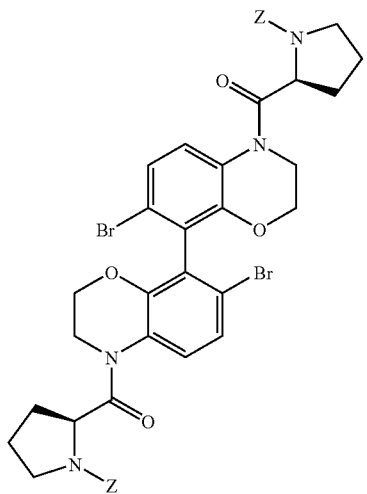

(16), Z is benzyloxycarbonyl 37.44 g of compound 15 and 36.1 ml of Hünig base are stirred in 300 ml of dichloromethane. While cooling (0-5° C.), a solution of 51.75 g of (S)-Z-proline acid chloride in 100 ml of dichloromethane is added dropwise. The mixture is stirred overnight and the reaction mixture is washed with saturated NaHCO$_3$ solution and 1N HCl. The organic phases are dried over sodium sulfate, stirred with activated carbon and a little silica gel, filtered with suction and evaporated on a rotary evaporator. This gives 78 g of 16 as a light-brown foam.

Rf=0.33 (CH$_2$Cl$_2$/acetone 9:1).

e) Preparation of

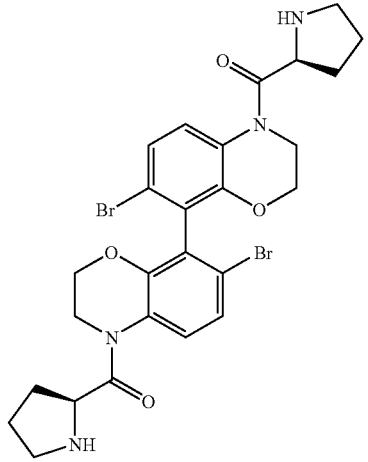

Diastereomers (17) and (18)

130 ml of HBr/glacial acetic acid 33% are added to a solution of 76.8 g of compound 16 in 250 ml of glacial acetic acid. As soon as the mixture stops foaming (15 minutes), it is evaporated on a rotary evaporator, subsequently coevaporated with toluene and finally stirred with acetonitrile at 80° C. for 20 minutes. At RT, the solidified mass is crushed well and filtered off with suction. This gives the dihydrobromide of the compounds 17/18 which is substantially free of benzyl bromide. The amine is set free by extraction with aqueous Na$_2$CO$_3$ solution in the presence of CH$_2$Cl$_2$/MeOH 9:1. Column chromatography on 1.1 kg of silica gel 40-63 µm, (eluent: CH$_2$Cl$_2$/methanol/NEt3 100:10:3) gives the two pure diastereomers 17 and 18 in virtually quantitative yield.

$^1$H NMR 18 (DMSO-d6): 7.90 (s, 2H), 7.20 (d, 2H), 4.23 (q, 4H), 4.06 (m, 4H), 3.73 (m, 2H), 2.95 (m, 2H), 2.72 (m, 2H), 1.98-(m, 2H), 1.82.(m, 2H), 1.69 (m, 4H). R$_f$ of 17=0.35; R$_f$ of 18=0.20 (CH$_2$Cl$_2$/methanol/NH$_4$OH 25%=80:10:1)

f) Preparation of

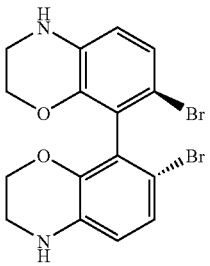

(19)

17.1 ml of aqueous sodium hydroxide solution (50%) are added to a solution of 20.0 g of compound 18 in 200 ml of methanol and 20 ml of THF and the reaction mixture is refluxed for 1 hour. The reaction mixture is evaporated on a rotary evaporator. This results in the product crystallizing. This is filtered off with suction and washed with methanol. The desired product 19 is obtained as pink crystalline needles.

$R_f$=0.45 (CH$_2$Cl$_2$/isopropanol 20:1).

g) Preparation of

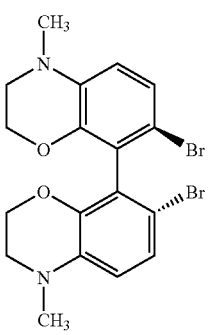

(12)

4 ml of aqueous hydrochloric acid 37% and 7.5 ml of formalin 36% are added to a suspension of 10.53 g of compound 19 in 130 ml of methanol and 25 ml of THF while stirring. While cooling (0-5° C.), 3.4 g of sodium cyanoborohydride are added a little at a time and the mixture is subsequently stirred at RT for 2 hours. The reaction mixture is evaporated on a rotary evaporator. It is then extracted twice with dichloromethane in the presence of water. The organic phases are dried over sodium sulfate and evaporated to dryness on a rotary evaporator. Drying over blue gel at 70° C. in a high vacuum gives 20 as a white foam.

$^1$H NMR (CDCl$_3$): 7.13 (d, 2H), 6.57 (d, 2H), 4.23 (t, 4H), 3.28 (m, 4H), 2.90 (s, 6H).

EXAMPLE A3

Preparation of

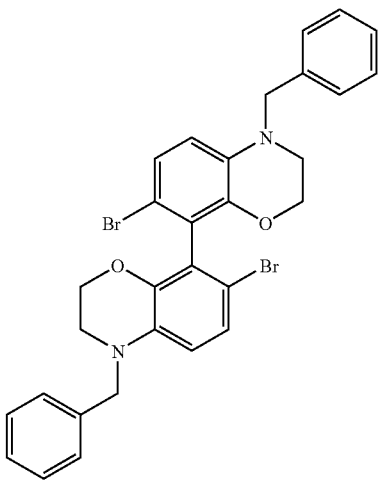

(20)

0.5 g of compound 15 is stirred with 442 µl of Hünig base and 307 µl of benzyl bromide in 10 ml of DMF at 60° C. for 10 hours. The reaction mixture is extracted with water/diethyl ether, the organic phases are dried over sodium sulfate and evaporated on a rotary evaporator. The crude product is chromatographed on 14 g of silica gel 40-63 µm (eluent: petrolium ether/ethyl acetate 4:1). Digestion with methanol gives 20 as a brownish foam.

$^1$H NMR (CDCl$_3$): 7.30 (m, 10H), 7.08 (d, 2H), 6.60 (d, 2H), 4.46 (s, 4H), 4.23 (t, 4H), 3.37 (m, 4H).

EXAMPLE A4

Preparation of

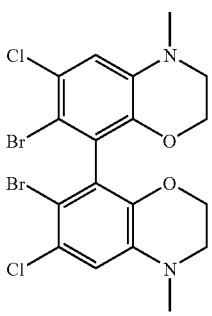

(21)

a) Preparation of

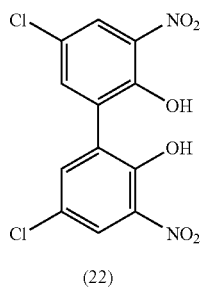 → 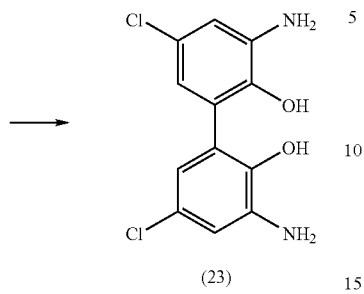

A solution of 6 g (19.4 mmol) of compound 22 is hydrogenated by means of 1 bar of hydrogen in the presence of 1.35 g of Raney nickel (wetted with ethanol) at room temperature while stirring intensively. After 1.5 hours, the hydrogenation stops (no longer any uptake of hydrogen). The catalyst is filtered off and the solvent is distilled off on a rotary evaporator. This gives a brownish crystalline product in quantitative yield. The hydrogenation solution can be used for the next step even without work-up.

$^1$H-NMR (DMSO): 6.64 (d), 6.35 (d).

b) Preparation of

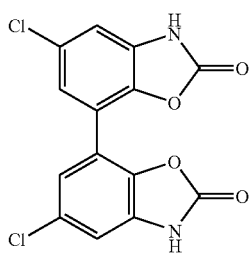

Firstly 20.2 g (0.2 mol) of triethylamine and subsequently at 0-5° C. a solution of 10.4 g (35 mmol) of triphosgene are added dropwise to a solution of 14.2 g (50 mmol) of compound 23 in 300 ml of THF over a period of 15 minutes while stirring under argon. After stirring for another 30 minutes, the reaction mixture is admixed with 300 ml of water and the THF is subsequently distilled off on a rotary evaporator. The resulting dark suspension is filtered, the solid is washed with water and dried at 60° C. under reduced pressure in a drying oven. The dry brown crude product is admixed with 100 ml of acetonitrile and stirred at room temperature for one hour. The product is filtered off, washed with acetonitrile and dried. This gives 14.5 g of brown product (yield: 86%).

$^1$H-NMR (DMSO): 12.1 (s, broad, 2H), 7.43 (d, 2H), 7.25 (d, 2H).

c) Preparation of

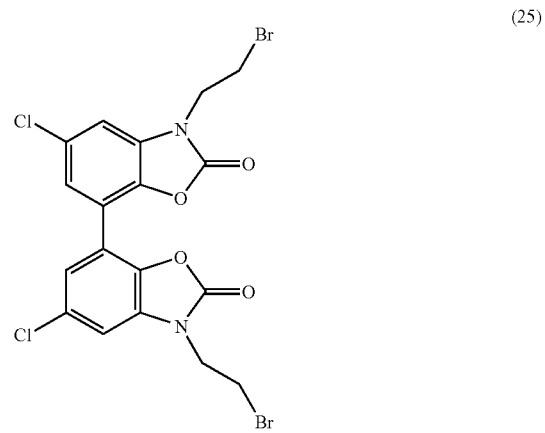

35.7 g (190 mmol) of 1,2-dibromoethane and 10.8 g (78 mmol) of potassium carbonate (powder) are added to 6.5 g (19.4 mmol) of compound 24 in 65 ml of DMF and the mixture is stirred at room temperature for 48 hours. The DMF is subsequently distilled off at 10 mbar on a rotary evaporator. The residue is stirred with water, filtered off, washed with water and dried at 40° C. under reduced pressure for 3 hours in a drying oven. This gives a violet-brown crude product which is stirred in 50 ml of acetonitrile for 30 minutes. The resulting, distinctly lighter-colored, fine suspension is filtered, the solid is washed with acetonitrile and the product is finally dried under reduced pressure on a rotary evaporator. This gives 7.3 g of product (yield: 69%).

$^1$H-NMR (DMSO): 7.77 (d, 2H), 7.52 (d, 2H), 4.33 (t, 4H), 3.88 (t, 4H).

e) Preparation of

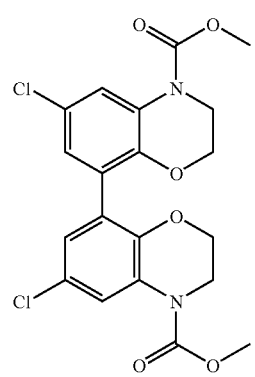

A mixture of 2.55 g (4.6 mmol) of compound 25 and 1.05 g (18.5 mmol) of sodium methoxide (95%) in 50 ml of methanol is refluxed while stirring for 1.5 hours. The resulting dark solution is subsequently evaporated to dryness on a rotary evaporator. The residue is shaken in 100 ml of methylene chloride and 20 ml of water. The organic phase is washed twice with water and the aqueous phases are extracted once with methylene chloride. The organic phases are dried over sodium sulfate and evaporated and dried under reduced pressure on a rotary evaporator. This gives 2.07 g of violet foam (yield: 99%).

$^1$H-NMR (DMSO): 7.85 (s, broad, 2H), 6.84 (d, 2H), 4.10 (t, 4H) 3.82 (t, 4H), 3.78 (s, 6H).

f) Preparation of

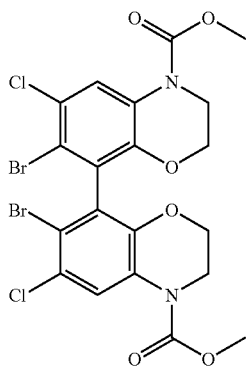

(27)

20 mg of iron powder and subsequently 2.86 g (17.9 mmol) of bromine are added to a solution of 3.25 g (7.16 mmol) of compound 26 in 75 ml of dichloromethane at room temperature. After one hour, a further 0.3 g of bromine is added and the mixture is stirred for another one hour. The reaction solution is decanted off from the dark iron salt residue, diluted with methylene chloride and washed three times with water. The organic phase is dried over sodium sulfate and evaporated under reduced pressure on a rotary evaporator. This gives 3.77 g of yellow crystalline material (yield 86%). If required, this crude product can be purified further by digesting it in 100 ml of methylene chloride/50 ml of ethyl acetate, distilling off the methylene chloride at 600 mbar on a rotary evaporator, filtering off the solid product which has precipitated and washing it with ethyl acetate.

$^1$H-NMR (CDCl$_3$): 8.15 (s, broad, 2H), 4.08 (t, 4H), 3.81 (t, 4H), 3.78 (s, 6H).

g) Preparation of

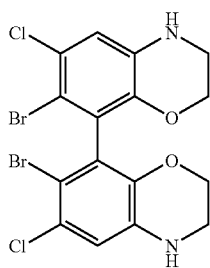

(28)

A mixture of 3.05 g (5 mmol) of compound 27, 50 ml of methanol and 50 ml of THF is admixed with 20 ml of aqueous sodium hydroxide solution (15%) under argon and the mixture is refluxed for 2.5 hours. The methanol and the THF are then distilled off on a rotary evaporator. The light-colored suspension which remains is filtered, the solid is washed with water and dried at 50° C. under reduced pressure in a drying oven. This gives 2.36 g of crystalline product (yield: 95%).

$^1$H-NMR (DMSO): 6.79 (s, 2H), 6.28 (s, 2H), 4.11-3.91 (m, 4H), 3.26 (m, 4H).

h) Preparation of

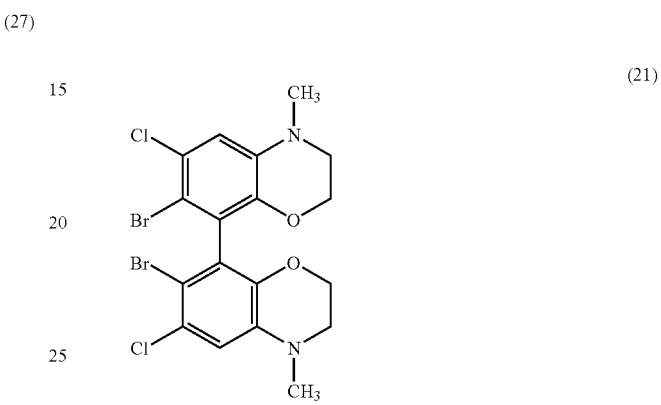

(21)

1.52 ml (20 mmol) of formaldehyde solution (36%), 0.215 ml (10 mmol) of concentrated hydrochloric acid (37%) and 725 mg (11 mmol) of cyanoborohydride are added a little at a time to 1.98 g (4 mmol) of compound 28 in 50 ml of methanol and 5 ml of THF while stirring and the mixture is stirred overnight. The methanol and the THF are distilled off on a rotary evaporator, the suspension is diluted with water, and mixed with sodium bicarbonate solution and stirred, filtered and the solid is washed with water. Drying at 40-50° C. in a drying oven gives 2.05 g of colorless, crystalline product (yield: 98%).

$^1$H-NMR (CDCl$_3$): 6.72 (s, 2H), 4.13 (t, 4H), 3.33-3.13 (m, 4H), 2.85 (s, 6H)

B) Preparation of Diphosphine Ligands

EXAMPLE B1

Preparation of the Diphosphine Ligand (29), Ph is phenyl

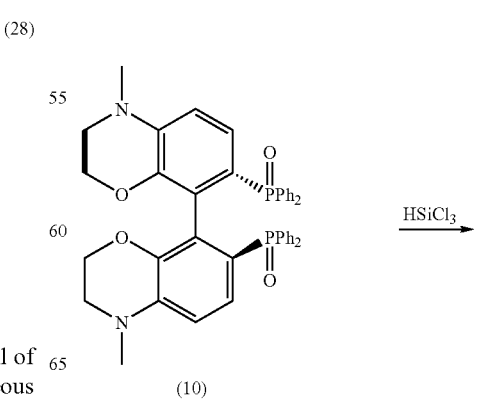

(10)

-continued

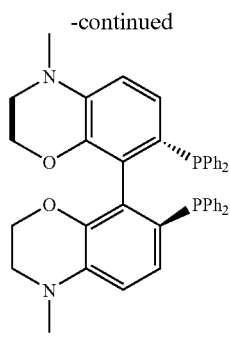

(29)

200 mg of the diphosphine oxide (10), 5 ml of toluene, 1.6 ml of trichlorosilane and 0.43 ml of triethylamine are placed in a steel autoclave, the autoclave is closed and the reaction mixture is stirred at 110° C. for 12 hours. After cooling to RT, a little ice is added and the mixture is extracted with a saturated aqueous NaHCO$_3$ solution and methylene chloride. The organic phase is dried over sodium sulfate and the solvent is then removed on a rotary evaporator. The product (12) is purified by flash chromatography (silica gel Merck 60; eluent: toluene containing 2% of triethylamine) and is obtained as a white powder.

$^1$H-NMR (300 MHz, CDCl$_3$): 7.28-6.95 (20H, m); 6.55 (4H, m,); 3.73-3.64 (2H, $^2$J=10.5, m); 3.50 (2H, ddd, $^3$J=7.5, 3.5); 3.16 (2H, ddd, $^2$J=10.5, $^3$J=7.5, 3.5); 2.81-2.78 (2H, m); 2.78 (6H, s). $^{31}$P-NMR (121.5 MHz, CDCl$_3$): −14.9.

EXAMPLE B2

Preparation of the Diphosphine Ligand 30

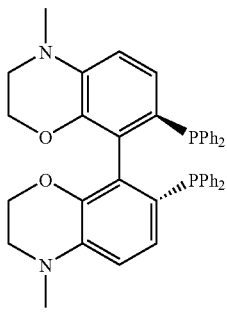

(30)

A solution of 10.23 g of compound 12 in 140 ml of dry THF and 7.9 ml of dry hexamethylphosphoramide (HMPA) is stirred with 2 g of molecular sieves 4A under argon for 1 hour. 60 ml of tert-butyllithium (1.5 M in pentane) are subsequently added dropwise at from −76° to −64° C. and the mixture is stirred at −75° C. for 12 minutes. A solution of 8.1 ml of diphenylchlorophosphine in 25 ml of THF is then added dropwise over a period of 1.5 minutes, resulting in the temperature rising to −43° C. The mixture is allowed to warm to RT and the reaction mixture is then evaporated on a rotary evaporator, extracted twice between water and dichloromethane, the organic phases are dried over sodium sulfate and evaporated on a rotary evaporator. The crude product is chromatographed with exclusion of light on 250 g of silica gel 40-63 µm (covered with 30g Alox IV), eluent: toluene/MTB 98:2 containing 1% of NEt$_3$ and a little BHT. The pure fractions are evaporated on a rotary evaporator. Any residual racemate can be crystallized away by dissolution in 20 ml of ethyl acetate/diethyl ether and seeding with racemate, since the optically pure product is much more readily soluble in this solvent mixture than is the racemate. The product is then digested with hot isopropanol. After cooling, it is crushed. The powder obtained in this way is filtered off and dried at 70° C. in a high vacuum. This gives the product 30 as a yellowish powder which is stable in air.

$^1$H NMR (CDCl$_3$): 7.0-7.4 (m, 20H), 6.60 (t, 4H), 3.75 (m, 2H), 3.26 (m, 4H), 2.82 (m, 2H), 2.80 (s, 6H). $^{31}$P (CDCl$_3$): −15.3 (s).

EXAMPLE B3

Preparation of the Diphosphine Ligand 31

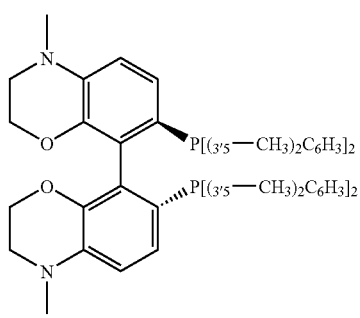

(31)

The procedure of Example B2 is repeated using di-3,5-xylylchlorophosphine in place of diphenylchlorophosphine. This gives the diphosphine 31 as a yellowish powder having a melting point of 143-150° C.

$^1$H NMR (C$_6$D$_6$): 7.47 (d, 4H), 7.36 (d, 4H), 7.24 (dd, 2H), 6.88 (d, 4H), 6.56 (d, 2H), 3.73 (m, 2H), 3.46 (m, 2H), 2.72 (m, 2H), 2.40 (m, 2H), 2.31 (s, 6H), 2.20 (s, 24H). $^{31}$P (C$_6$D$_6$): −14.5 (s).

EXAMPLE B4

Preparation of the Diphosphine Ligand 32

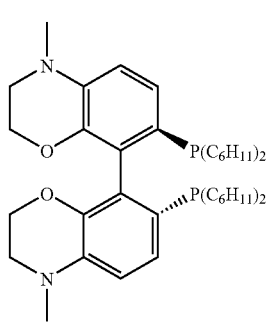

(32)

The procedure of Example B2 is repeated using dicyclohexylchlorophosphine in place of diphenylchlorophosphine. This gives the compound 32 as a beige powder.

R$_f$=0.63 (CH$_2$Cl$_2$/methanol/NH$_4$OH 25% 100:10:1).

ESI-MS: M+H 689.

EXAMPLE B5

Preparation of the Diphosphine Ligand 33

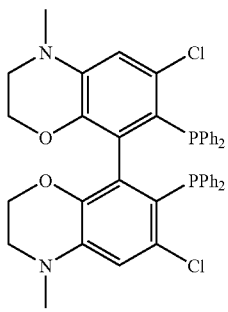
(33)

The procedure of Example B2 is repeated using compound 21 and diphenylchlorophosphine to give compound 33.

EXAMPLE B6

Preparation of the Diphosphine Ligand 34

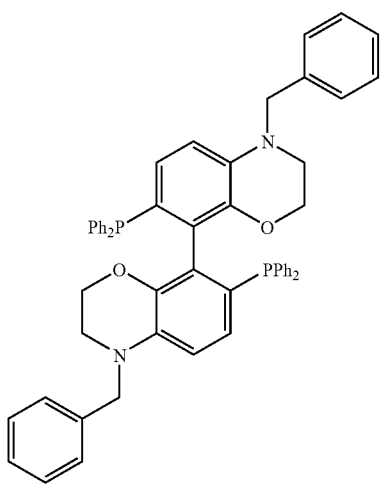
(34)

The procedure of Example B2 is repeated using compound 20 and diphenylchlorophosphine.

$^1$H NMR (CDCl$_3$): 7.0-7.4 (m, 30H), 6.50-6.70 (m, 4H), 4.40 (q, 4H), 3.75 (m, 2H), 3.26 (m, 4H), 2.88 (m, 2H). $^{31}$P (CDCl$_3$): −15.1 (s). ESI-MS: M+H 817.

C) Preparation of Metal Complexes

EXAMPLE C1

Preparation of a Ruthenium Complex 1.47 mg (0.0015 mmol) of [RuI$_2$(p-cumene)]$_2$ and 2.14 mg (0.0032 mmol) of diphosphine ligand (29) from Example B1 are introduced into a Schlenk vessel filled with an argon atmosphere. 5 ml of ethanol (degassed) are subsequently added and the solution is stirred at room temperature for 10 minutes. The solution is used directly for the hydrogenation.

EXAMPLE C2

Preparation of a Ruthenium Complex 6.3 mg (0.0063 mmol) of [RuI$_2$(p-cumene)]$_2$ and 8.8 mg (0.0133 mmol) of diphosphine ligand (29) from Example B1 are introduced into a Schlenk vessel filled with an argon atmosphere. 5 ml of ethanol (degassed) are subsequently added and the solution is stirred at room temperature for 10 minutes. The solution is used directly for the hydrogenation.

EXAMPLE C3

Preparation of a Ruthenium Complex 11.4 mg (0.0115 mmol) of [RuI$_2$(p-cumene)]$_2$ and 15.9 mg (0.024 mmol) of diphosphine ligand (29) from Example B1 are introduced into a Schlenk vessel filled with an argon atmosphere. 20 ml of ethanol (degassed) are subsequently added and the solution is stirred at room temperature for 10 minutes. The solution is used directly for the hydrogenation.

EXAMPLE C4

Preparation of a Water-Soluble Rhodium Complex

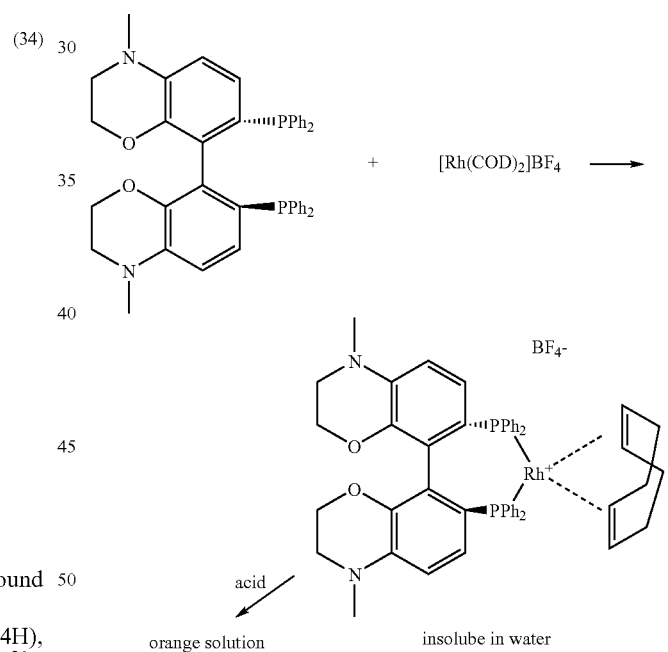

11.6 mg (0.0175 mmol) of ligand (29) and 6.9 mg (0.017 mmol) of [Rh(COD)$_2$]BF$_4$ are placed under argon in a Schlenk vessel provided with a magnetic stirrer and dissolved in 0.9 ml of degassed methanol. After stirring for 10 minutes, the methanol is taken off under reduced pressure at room temperature. 2 ml of degassed water are added to the red, solid Rh complex which remains and the mixture is stirred intensively. The complex does not dissolve and the water remains colorless. While stirring, methanesulfonic acid is subsequently added slowly. This results in the complex beginning to dissolve. Addition of 320 microliters of methanesulfonic acid results in a clear orange solution by means of which hydrogenations can be carried out in aqueous solution.

D) Use Examples

EXAMPLE D1

Hydrogenation of ethyl 3-ketobutyrate

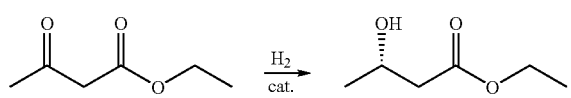

30 g of ethyl acetoacetate, 5 ml of degassed ethanol and 0.9 ml of 1 N HCl are introduced in succession into a Schlenk vessel filled with argon. This solution and the catalyst solution from Example C1 are then transferred in succession by means of a steel capillary into a 50 ml steel autoclave filled with argon. The s/c (substrate/catalyst) ratio is 75 000. The autoclave is closed and a pressure of 50 bar is set using 4 flushing cycles (pressurization with 20 bar of hydrogen). The autoclave is then heated to 80° C., and after 30 minutes the reaction pressure is set to 80 bar. The autoclave is stirred for 19 hours. The heating is subsequently switched off and the autoclave is cooled to room temperature. After depressurization, a reddish reaction solution is isolated. The conversion is >98% (determined by means of GC and $^1$H-NMR). Removal of the solvent on a rotary evaporator gives a quantitative yield of ethyl (R)-3-hydroxybutyrate having an enantiomeric purity of 97.1% ee. (determined by means of GC after reaction with trifluoroacetic anhydride; column: Lipodex E, 50 m).

EXAMPLE D2

Hydrogenation of ethyl benzoylacetate

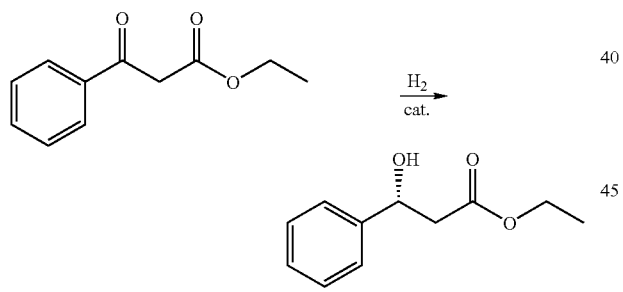

0.498 g (2.53 mmol) of ethyl benzoylacetate, 5 ml of degassed ethanol and 60 µl of 1N HCl are introduced in succession into a Schlenk vessel filled with argon. This solution and the catalyst solution from Example C2 are then transferred in succession by means of a steel capillary into a 50 ml steel autoclave filled with argon. The s/c (substrate/catalyst) ratio is 200. The autoclave is closed and a pressure of 50 bar is set using 4 flushing cycles (pressurization with 20 bar of hydrogen). The autoclave is then heated to 80° C., and after 30 minutes the reaction pressure is set to 80 bar. The autoclave is stirred for 21 hours. The heating is subsequently switched off and the autoclave is cooled to room temperature. After depressurization, a reddish reaction solution is isolated. The conversion is >98% (determined by means of GC and $^1$H-NMR). Removal of the solvent on a rotary evaporator gives a quantitative yield of ethyl (S)-3-hydroxyphenylpropionate having an enantiomeric purity of 98% ee (determined by means of HPLC; column: Chiralcel OD-H, 250 mm, hexane/i-propanol 93:7, flow rate: 0.8 ml/min.).

COMPARATIVE EXAMPLE

The procedure of Example D2 is repeated using 7.73 mg (0.0133 mmol) of (R)-MeObiphep in place of the ligand (29). The conversion is >98%. Removal of the solvent on a rotary evaporator gives a quantitative yield of ethyl (S)-3-hydroxyphenylpropionate having an enantiomeric purity of 92% ee.

EXAMPLE D3

Hydrogenation of acetylacetone

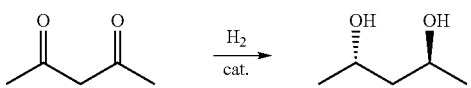

0.253 g (2.53 mmol) of acetylacetone, 5 ml of degassed ethanol and 60 µl of 1N HCl are introduced in succession into a Schlenk vessel filled with argon. This solution and the catalyst solution from Example C2 are then transferred in succession by means of a steel capillary into a 50 ml steel autoclave filled with argon. The s/c (substrate/catalyst) ratio is 200. The autoclave is closed and a pressure of 50 bar is set using 4 flushing cycles (pressurization with 20 bar of hydrogen). The autoclave is then heated to 80° C., and after 30 minutes the reaction pressure is set to 80 bar. The autoclave is stirred for 16 hours. The heating is subsequently switched off and the autoclave is cooled to room temperature. After depressurization, a reddish reaction solution is isolated. The conversion is >98% (determined by means of GC and $^1$H-NMR). Removal of the solvent on a rotary evaporator gives a quantitative yield of (2R,4R)-pentane-2,4-diol having an enantiomeric purity of 99% ee (ratio of dl:meso; 98:2; determined by means of GC after reaction with trifluoroacetic anhydride; column: Lipodex E, 50 m).).

EXAMPLE D4

Hydrogenation of ethyl benzoylacetate

The procedure of Example D2 is repeated using 10.3 mg (0.0133 mmol) of the diphosphine (31) from Example B3 in place of the ligand (29). The substrate solution is used without addition of HCl. The conversion is quantitative (determined by means of GC and $^1$H-NMR). Removal of the solvent on a rotary evaporator gives a quantitative yield of ethyl (S)-3-hydroxyphenylpropionate having an enantiomeric purity of 98.2% ee.

EXAMPLE D5

Hydrogenation of ethyl cyclohexyl-3-ketopropionate

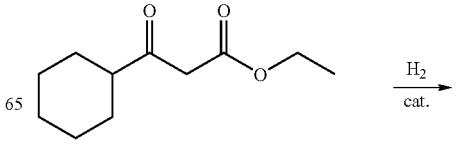

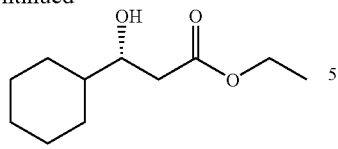

The procedure of Example D2 is repeated using 10.3 mg (0.0133 mmol) of the diphosphine (31) from Example B3 in place of the ligand (29). The substrate solution comprises 0.502 mg (2.53 mmol) of ethyl cyclohexyl-3-ketopropionate, 60 ml of 1N HCl and 5 ml of ethanol. The conversion is quantitative (determined by means of GC and $^1$H-NMR). Removal of the solvent on a rotary evaporator gives a quantitative yield of ethyl (S)-3-hydroxy-3-cyclohexylpropionate having an enantiomeric purity of 96.4% ee.

EXAMPLE D6

Hydrogenation of acetylacetone

The procedure of Example D3 is repeated using 10.3 mg (0.0133 mmol) of the diphosphine (31) from Example B3-in place of the-ligand (29). The conversion is >98% (determined by means of GC and $^1$H-NMR). Removal of the solvent on a rotary evaporator gives a quantitative yield of (2R,4R)-pentane-2,4-diol having an enantiomeric purity of 99.4% ee (ratio of dl:meso; 98.5:1.5).

The invention claimed is:
1. A compound of the formula I,

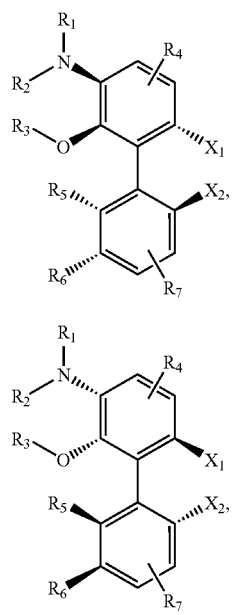

where
$X_1$ and $X_2$ are each, independently of one another, secondary phosphino;
$R_1$ and $R_2$ are each, independently of one another, hydrogen, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, or
$R_1$ and $R_2$ together are $C_4$-$C_8$-alkylene, 3-oxapentyl-1,5-ene, —(CH$_2$)$_2$—NH—(CH$_2$)$_2$— or —(CH$_2$)$_2$—N(C$_1$-C$_4$alkyl)-(CH$_2$)$_2$—,
$R_3$ is hydrogen, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, or
$R_1$ is as defined above and $R_2$ and $R_3$ together are $C_2$-$C_8$-alkylidene, $C_4$-$C_8$-cycloalkylidene, $C_1$-$C_4$-alkylene, $C_2$-$C_8$-alk-1,2-enyl, —C(O)— or a group of the formula

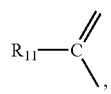

or
$R_1R_2N$ and $R_3O$ together are a group of the formula

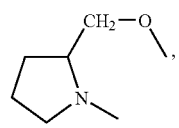

$R_4$ and $R_7$ are each, independently of one another, hydrogen, $C_1$-$C_4$-alkyl, $C_1$-$C_4$-alkoxy, F, Cl or trifluoromethyl,
$R_5$ is hydrogen, $R_4$ or an $R_3O$— group, where $R_3O$— groups in the two rings can be identical or different,
$R_6$ is hydrogen, $R_7$ or an $R_1R_2N$— group, where $R_1R_2N$— groups in the two rings can be identical or different,
$R_5$ and $R_6$ together are trimethylene, tetramethylene or —CH═CH—CH═CH—, and
$R_{11}$ is $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl,
where $R_1$, $R_2$, $R_3$, $R_4$ and $R_7$ are unsubstituted or substituted by $C_1$-$C_4$-alkyl, $C_1$-$C_4$-alkoxy, OH, F, Cl, Br, trifluoromethyl, $C_1$-$C_4$-hydroxyalkyl, —COOH, —SO$_3$H, —C(O)O—$C_1$-$C_4$-alkyl, —SO$_3$—$C_1$-$C_4$-alkyl, —C(O)—NH$_2$, —CONHC$_1$-$C_4$-alkyl, —CON(C$_1$-$C_4$-alkyl)$_2$, —SO$_3$—NH$_2$, —SO$_2$—NHC$_1$-$C_4$-alkyl, —SO$_3$—N(C$_1$-$C_4$-alkyl)$_2$, —O$_2$C—R$_8$, —O$_3$S—R$_8$, —NH—(O)C—R$_8$, —NH—O$_3$S—R$_8$, —NH$_2$, —NHR$_9$ or —NR$_9$R$_{10}$, where R$_8$ is hydrogen, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl or $C_7$-$C_{11}$-aralkyl, and R$_9$ and R$_{10}$ are each, independently of one another, $C_1$-$C_4$-alkyl, phenyl or benzyl or R$_9$ and R$_{10}$ together are tetramethylene, pentamethylene, 3-oxa-1,5-pentane or —(CH$_2$)$_2$—N(C$_1$-C$_4$-alkyl)-(CH$_2$)$_2$—.

2. The compound as claimed in claim 1, characterized in that $X_1$ is a —P(R)$_2$ group and $X_2$ is a —P(R')$_2$ group, where R and R' are each, independently of one another, a hydrocarbon radical which has from 1 to 20 carbon atoms and is unsubstituted or substituted by halogen, $C_1$-$C_6$-alkyl, $C_1$-$C_6$-haloalkyl, $C_1$-$C_6$-alkoxy, $C_1$-$C_6$-haloalkoxy, —CO$_2$-$C_1$-$C_6$-alkyl, (C$_6$H$_5$)$_3$Si or (C$_1$-$C_{12}$-alkyl)$_3$Si; or the radicals R and R' together are unsubstituted or $C_1$-$C_4$-alkyl- and/or $C_1$-$C_4$-alkoxy-substituted tetramethylene or pentamethylene.

3. The compound as claimed in claim 1, characterized in that it corresponds to the formula Ib,

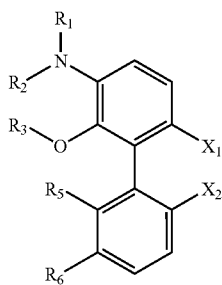

where $R_1$, $R_2$ and $R_3$ are each, independently of one another, $C_1$-$C_4$-alkyl, $R_5$ is hydrogen or an $OR_3$ group, $R_6$ is hydrogen or an —$NR_1R_2$ group, or $R_5$ and $R_6$ together are —CH=CH—CH=CH—, and $X_1$ and $X_2$ are secondary phosphino.

4. The compound as claimed in claim 1, characterized in that it corresponds to the formula Ic,

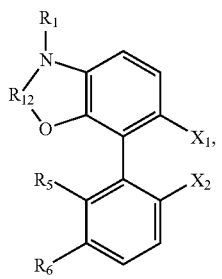

where $R_1$ $C_1$-$C_4$-alkyl, $R_5$ and $R_6$ are each hydrogen or $R_5$ and $R_6$ together are an —$NR_1$—$R_{12}$—O— group, $X_1$ and $X_2$ are secondary phosphino and $R_{12}$ is 1,2-ethylene, 1,2-ethenylene, —C(O)— or a group of the formula

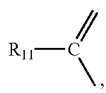

where $R_{11}$ is branched $C_3$-$C_8$-alkyl, $C_5$-$C_6$-cycloalkyl, phenyl or benzyl.

5. A process for preparing compounds of the formulae I and Ia,

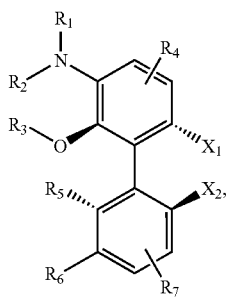

(I)

-continued

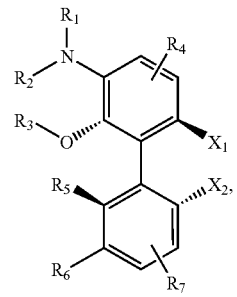

(Ia)

where $R_1$, $R_2$, $R_3$, $R_4$, $R_5$, $R_6$, $R_7$, $X_1$ and $X_2$ are as defined in claim 1, which comprises the steps:

a) halogenation of a compound of the formula VI

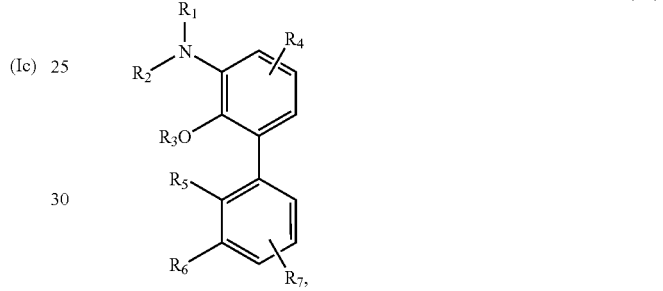

(VI)

where $R_1$, $R_2$, $R_3$, $R_4$, $R_5$, $R_6$ and $R_7$ are as defined above, or $R_1$ is a protective group which can be split off and $R_2$ is hydrogen or is as defined above, or $R_3$ is a protective group which can be split off, or $R_1$ and $R_3$ together form a protective group which can be split off and $R_2$ is hydrogen or is as defined above, by means of chlorine, bromine or iodine to form a compound of the formula VII

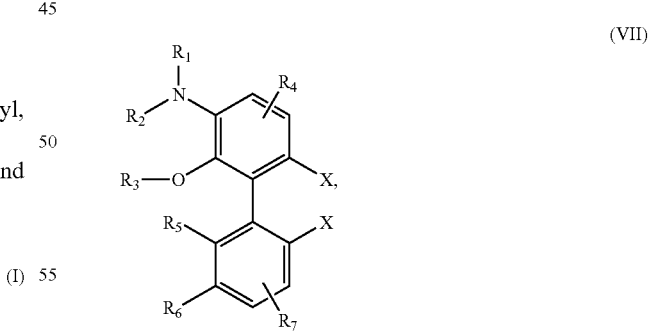

(VII)

where X is chlorine, bromine or iodine, b) if appropriate to introduce the radicals $R_2$ and $R_3$, removal of the protective groups to form OH-functional and NH-functional groups and replacement of the H atoms in the OH-functional and NH-functional groups by means of a reagent $R_2$—$X_2$, $R_3$—$X_2$ or $X_2$—$R_{13}$—$X_2$, where $X_2$ is a leaving group and $R_{13}$ is 1,2-alkylene or 1,2-cycloalkylene, to produce compounds of the formula VII, and if appropriate resolution of the racemates of the formula VII to give the enantiomers of the formulae VIIa and VIIb

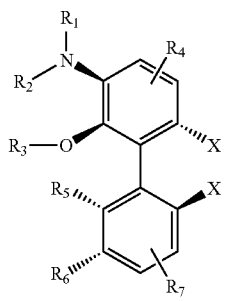

VIIa

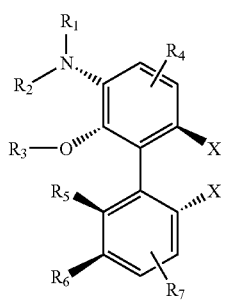

VIIb c) metalation of the compounds of the formula VII, for example by means of a lithium alkyl, and subsequent reaction with a halophosphine of the formula $X_3$—PRR ($X_3$ is halogen) in the presence of a lithium alkyl to give diphosphines of the formula VIII, or with a halophosphine oxide of the formula $X_3$—P(O)RR to give diphosphine oxides of the formula IX, or with a phosphonate of the formula $X_3P(O)(OR°)_2$ to give phosphonates of the formula IXa:

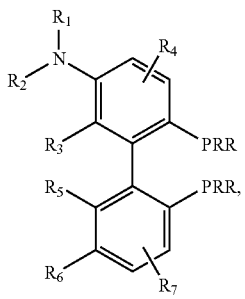

(VIII)

d) oxidation of the phosphine groups in compounds of the formula VIII by means of an oxidant to form compounds of the formula IX,

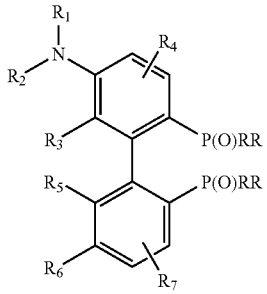

(IX)

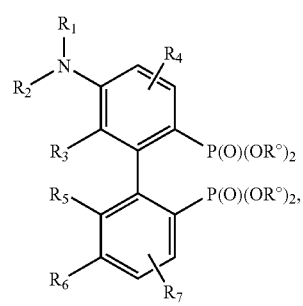

(IXa)

e) if a recemic starting material of the formula VII is used resolution of the racemates of the formula VIII to give the enantiomers Ia and Ib, or resolution of the racemates of the formula IX to give the enantiomers of the formulae X and Xa, or resolution of the racemates of the formula IXa to give the enantiomers of the formulae Xb and Xc, and reaction of Xb and Xc with R—Mg—X to form phosphine oxides of the formula X and Xa,

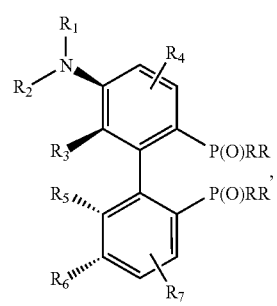

(X)

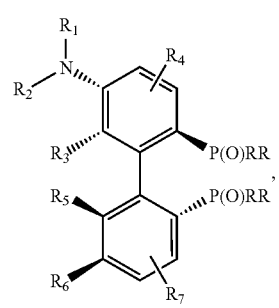

(Xa)

-continued

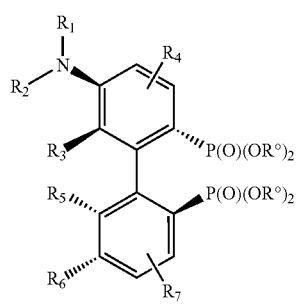 (Xb)

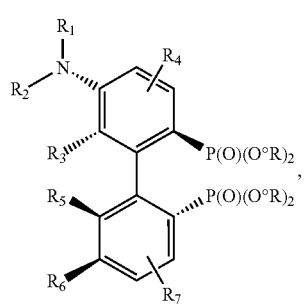 (Xc)

f) and reduction of the phosphine oxide group in the compounds of the formulae Xa and Xb to produce compounds of the formulae I and Ia.

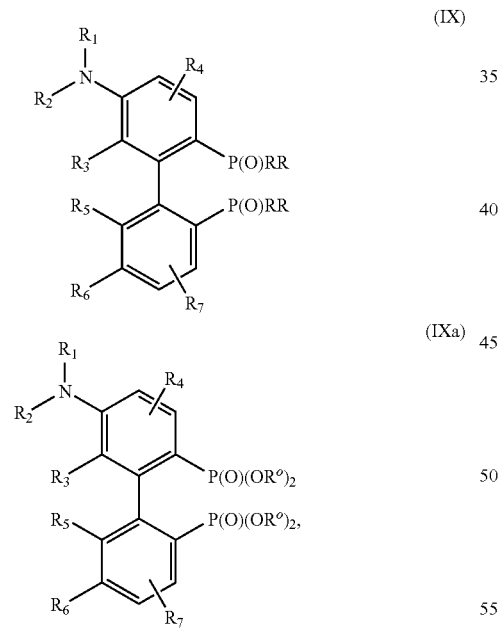 (IX)

(IXa)

-continued

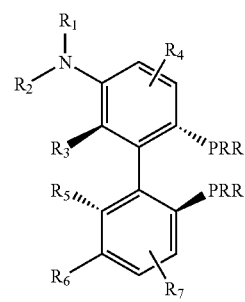 (I)

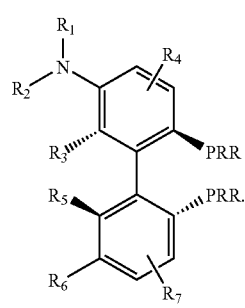 (Ia)

6. A compound of the formula VII in the form of the racemate, optically enriched or optically pure form,

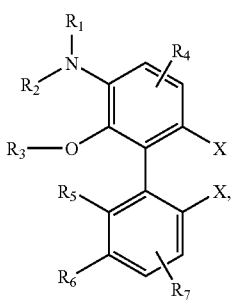 (VII)

where $R_1$, $R_2$, $R_3$, $R_4$, $R_5$, $R_6$ and $R_7$ are as defined in claim 1, or $R_2$ is a protective group which can be split off or $R_2$ and $R_3$ together form a protective group which can be split off and $R_1$, $R_3$, $R_4$, $R_5$, $R_6$ and $R_7$ or $R_1$, $R_4$, $R_5$, $R_6$ and $R_7$ are as defined in claim 1, and X is chlorine, bromine or iodine.

* * * * *